United States Patent [19]
Feist

[11] Patent Number: 6,142,985
[45] Date of Patent: Nov. 7, 2000

[54] ABSORBENT ARTICLES HAVING Z-FOLDED BARRIER CUFFS PROVIDING IMPROVED FIT AND CONTAINMENT

[75] Inventor: Barry Robert Feist, Cincinnati, Ohio

[73] Assignee: The Procter & Gamble Company, Cincinnati, Ohio

[21] Appl. No.: 08/389,086

[22] Filed: Feb. 14, 1995

Related U.S. Application Data

[63] Continuation of application No. 08/071,899, Jun. 3, 1993, abandoned.

[51] Int. Cl.[7] .................................................. A61F 13/15
[52] U.S. Cl. ............................... 604/385.28; 604/385.29; 604/385.3
[58] Field of Search ........................... 604/358, 365–366, 604/385.1–387

[56] References Cited

U.S. PATENT DOCUMENTS

| | | | |
|---|---|---|---|
| 4,040,423 | 8/1977 | Jones, Sr. | 128/287 |
| 4,041,950 | 8/1977 | Jones, Sr. | 128/287 |
| 4,490,148 | 12/1984 | Beckestrom | 604/385 |
| 4,695,278 | 9/1987 | Lawson | 604/385.2 |
| 4,704,115 | 11/1987 | Buell | 604/385 A |
| 4,704,116 | 11/1987 | Enloe | 604/385 |
| 4,738,677 | 4/1988 | Foreman | 604/385 R |
| 4,834,740 | 5/1989 | Suzuki et al. | 604/385.2 |
| 4,900,317 | 2/1990 | Buell | 604/385.2 |
| 4,909,803 | 3/1990 | Aziz et al. | 604/385.2 |
| 5,021,051 | 6/1991 | Hiuke | 604/385.2 |
| 5,026,364 | 6/1991 | Robertson | 601/385.2 |
| 5,167,653 | 12/1992 | Fgaue et al. | 604/388.2 |
| 5,171,391 | 12/1992 | Chmielewski et al. | 601/358 |

FOREIGN PATENT DOCUMENTS

| | | |
|---|---|---|
| 2152950 | 6/1990 | Japan . |
| 2174845 | 7/1990 | Japan . |
| 4012751 | 1/1992 | Japan ...................................... 604/387 |
| 2250921 | 6/1992 | United Kingdom ................ 604/385.1 |
| 9309739 | 5/1993 | WIPO . |

*Primary Examiner*—John G. Weiss
*Assistant Examiner*—K. M. Reichle
*Attorney, Agent, or Firm*—David M. Weirich; Steven W. Miller; Jacobus C. Rasser

[57] ABSTRACT

A Z-folded barrier cuff is provided to allow both sufficient lateral spacing of the barrier cuffs for the genitals in the front and for BM containment in the back as well as sufficient cuff height in the crotch area for good fit into the leg crease and good containment of body exudates. The barrier cuff is Z-folded by folding a first portion back upon itself such that a first segment and a second segment is formed. A second portion is folded laterally inwardly back upon itself such that a third segment is formed. Thus, the Z-folded barrier cuffs are properly laterally spaced in the crotch area and near the end edges while providing sufficient height to properly contain body exudates.

9 Claims, 13 Drawing Sheets

ABSORBENT ARTICLES HAVING Z-FOLDED BARRIER CUFFS PROVIDING IMPROVED FIT AND CONTAINMENT

This is a continuation of application Ser. No. 08/071,899, filed on Jun. 3, 1993, now abandoned.

FIELD OF THE INVENTION

The present invention relates to absorbent articles such as diapers, incontinent briefs, training pants, diaper holders and liners, sanitary hygiene garments, and the like, and more particularly, to absorbent articles providing sustained dynamic fit about the wearer.

BACKGROUND OF THE INVENTION

Infants and other incontinent individuals wear absorbent articles such as diapers to absorb and contain urine and other body exudates. Absorbent articles function both to contain the discharged materials and to isolate these materials from the body of the wearer and from the wearer's garments and bed clothing. Disposable absorbent articles having many different basic designs are known in the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elastic leg cuff disposable diaper which has achieved wide acceptance and commercial success.

However, absorbent articles have a tendency to sag or gap away from and to slide/slip down on the body of the wearer during use. This sagging/gapping and sliding/slipping is caused by the relative motions of the wearer as the wearer breathes, moves and changes position, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer.

Conventional disposable diapers are typically designed to fit high on the abdomen of the wearer and down on the thighs such that the diaper fits in the zones of the wearer that are subject to dynamic motion (and thus dynamic forces) during use. These dynamic motions and forces, especially by the abdomen bulging and contracting, tend to deform the materials making up the diaper and tend to push the diaper away from the body. Thus, the diaper tends to sag/gap away from the body. The closure system of the diaper is also typically designed to form a defined dimension of the waist and leg openings and a line of tension (imparts a tensile force along a line) about the wearer to secure the diaper on the wearer. However, this defined waist dimension created by the closure system cannot accommodate the changes in body dimension caused by wearer movement such that the diaper tends to slide/slip down on the wearer when the dimension of the abdomen of the wearer becomes smaller than the defined dimension formed by the closure. Further, when the abdominal dimension becomes larger than the defined dimension formed by the closure system, the body tends to push the diaper to a different position on the wearer (typically to a smaller dimension area which is lower than the point of initial fit) or the diaper tends to be so tight on the abdomen that the diaper can mark the skin or be uncomfortable to wear. Further, the absorbent core and other stiff nonelastic members of the diaper typically fit in the zones of the abdomen or legs that undergo such dynamic forces that the absorbent core is pushed downward or inward by the dynamic forces resulting in further gapping/sliding of the product on the wearer.

In order to more snugly fit absorbent articles about the wearer, certain commercially available absorbent articles have been provided with elastic features about the waist, hips, or legs. An example of a disposable diaper with an elastic waist feature which has achieved wide acceptance and commercial success is disclosed in U.S. Pat. No. 4,515,595 issued to Kievit and Osterhage on May 7, 1985. An example of a disposable diaper with an elastic leg cuff is disclosed in the previously mentioned U.S. Pat. No. 3,860,003. An example of a disposable diaper with elastic side panels to fit over the hips is disclosed in U.S. Pat. No. 4,857,067 issued to Wood, et al. on Aug. 15, 1989. The elastic features are designed to expand and contract with the wearer's motions and to maintain the fit of the absorbent article about the wearer during use (i.e., provide sustained dynamic fit).

However, it has been found that absorbent articles having elastic features also have a tendency to sag/gap and slide/slip during use.

Thus, it would be advantageous to provide an absorbent article that provides better fit, reduced leakage, and wearer comfort. It would further be advantageous to provide an absorbent article which has reduced sagging and gapping as well as reduced overall sliding/slipping of the absorbent article and/or the absorbent core on the wearer during use.

Therefore, it is an object of the present invention to provide an absorbent article having sustained dynamic fit about the wearer during use by reducing the sagging/gapping and sliding/slipping of the absorbent article on the wearer.

It is a further object of the present invention to provide an absorbent article providing increased comfort for the wearer by providing freedom of motion for the wearer and minimizing the effects of forces caused by wearer's movements on product stability.

It is also an object of the present invention to provide an absorbent article shaped to fit within the low motion zone of the wearer and/or to provide expansion of the absorbent article at those portions not fitting within the low motion zone.

It is a further object of the present invention to anchor the absorbent article about the perimeter of the low motion zone of the wearer to achieve sustained dynamic fit.

It is a still further object of the present invention to provide an absorbent article having an absorbent core shaped to fit in the low motion zone of the wearer so that the absorbent article has sustained dynamic fit during use.

It is also an object of the present invention to provide a closure system and containment assembly (chassis) design that anchor the absorbent core in the low motion zone of the wearer to enhance the sustained dynamic fit.

It is a still further object of the present invention to provide a containment assembly (chassis) design, closure system and an absorbent core shape cooperating to reduce sagging and gapping as well as overall sliding/slipping of the absorbent article during use.

These and other objects of the present invention will be more readily apparent when considered in reference to the following description and when taken in conjunction with the accompanying drawings.

SUMMARY OF THE INVENTION

The present invention provides absorbent articles such as diapers, incontinent briefs, training pants, diaper holders and liners, feminine hygiene garments, and the like, designed to provide sustained dynamic fit about the wearer during use as well as to improve the containment of body exudates and wearer comfort/mobility. Such an absorbent article has a containment assembly (chassis) comprising an outer covering layer typically comprising a liquid pervious topsheet and a liquid impervious backsheet, and an absorbent core associated with the outer covering layer. The absorbent core is preferably designed to fit within the low motion zone of the wearer (an anatomically low motion zone-fitting absorbent core) so that dynamic forces imparted by movements of the wearer on the absorbent core are minimized. The absorbent article is also provided with a closure system for anchoring the absorbent article on the wearer to sustain the dynamic fit of the absorbent article about the wearer throughout wearing. The closure system is designed so that a primary line of tension, fitting at an angle to the body, is formed to secure the absorbent article on a wearer in a manner that does not contribute to sagging or sliding of the diaper. The absorbent article preferably further comprises elastic features for fitting about the extremities of the wearer including elastic waist features, elastic leg cuffs, and elastic side panels that allow freedom of movement for the wearer as well as maintenance of forces about the body to sustain the fit of the absorbent article.

In a preferred embodiment of the present invention, the absorbent core is designed to fit within the low motion zone of the wearer (i.e., an anatomically low motion zone-fitting absorbent core). By designing the shape of the absorbent core to fit in the low motion zone of the wearer, the absorbent core is not likely to sag/gap or slip/slide during use since the absorbent core is positioned in the area of the wearer having little or no dynamic motions or forces tending to cause it to gap or slip. The absorbent core is provided with a front waist edge preferably having an arcuate concave shape to fit below or at the abdominal crease of the wearer. It is preferred that the curve of the front waist edge approximate the curve of the abdominal crease of the wearer such that the absorbent core will naturally fit into the low motion zone to maximize the comfort for the wearer. The absorbent core is also provided with arcuate concave side edges designed to fit in the leg creases of the wearer and to define a narrow crotch width which fits between the legs of the wearer. These leg cutouts are positioned farther forward in the absorbent core than the lateral centerline so that the front portion of the absorbent core is shorter in length to fit below the abdominal crease and to allow the absorbent core to fit higher over the buttocks and into the lumbar curve of the back. Preferably, the absorbent core is long enough in the back to fit upwardly over the buttocks of the wearer into the lumber curve of the back to anchor the back and to provide less gapping of the absorbent core in the back to further enhance BM containment.

The absorbent article is also preferably provided with a closure system for anchoring the absorbent article on the wearer. Preferably, the closure system provides a primary line of tension around the wearer that fits predominantly within the low motion zone to enhance the dynamic fit and to anchor the absorbent core in place so that it will not slip/slide during use. The primary line of tension established by the closure system is disposed at an angle on the wearer. In a preferred embodiment of the present invention, the closure system is provided with angled tapes, more preferably tapes of a specified design, to allow the wearer to easily form the "angled" primary line of tension about the wearer. The closure system is also provided with a landing member designed to enhance the opportunity for the user to establish this primary line of tension equally each time the closure system is used.

In an especially preferred embodiment of the present invention, the absorbent article additionally comprises elastic features positioned outside of the absorbent core to enhance the dynamic fit of the absorbent article about the wearer in those zones that undergo dynamic changes caused by the wearer's movements. In one embodiment, any zone outside of the absorbent core is elasticized to provide this type of fit. In an especially preferred embodiment, the absorbent article is provided with elastic waist features, elastic leg cuffs, and elastic side panels that provide elastic extensibility to provide greater freedom of movement for the wearer and a more comfortable and contouring fit by initially conformably fitting the diaper to the wearer and by sustaining this fit during use.

BRIEF DESCRIPTION OF THE DRAWINGS

While the specification concludes with claims particularly pointing out and distinctly claiming the subject matter which is regarded as forming the present invention, it is believed that the invention will be understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, training pants, diaper holders and liners, feminine hygiene garments, and the like.

Figure 1:
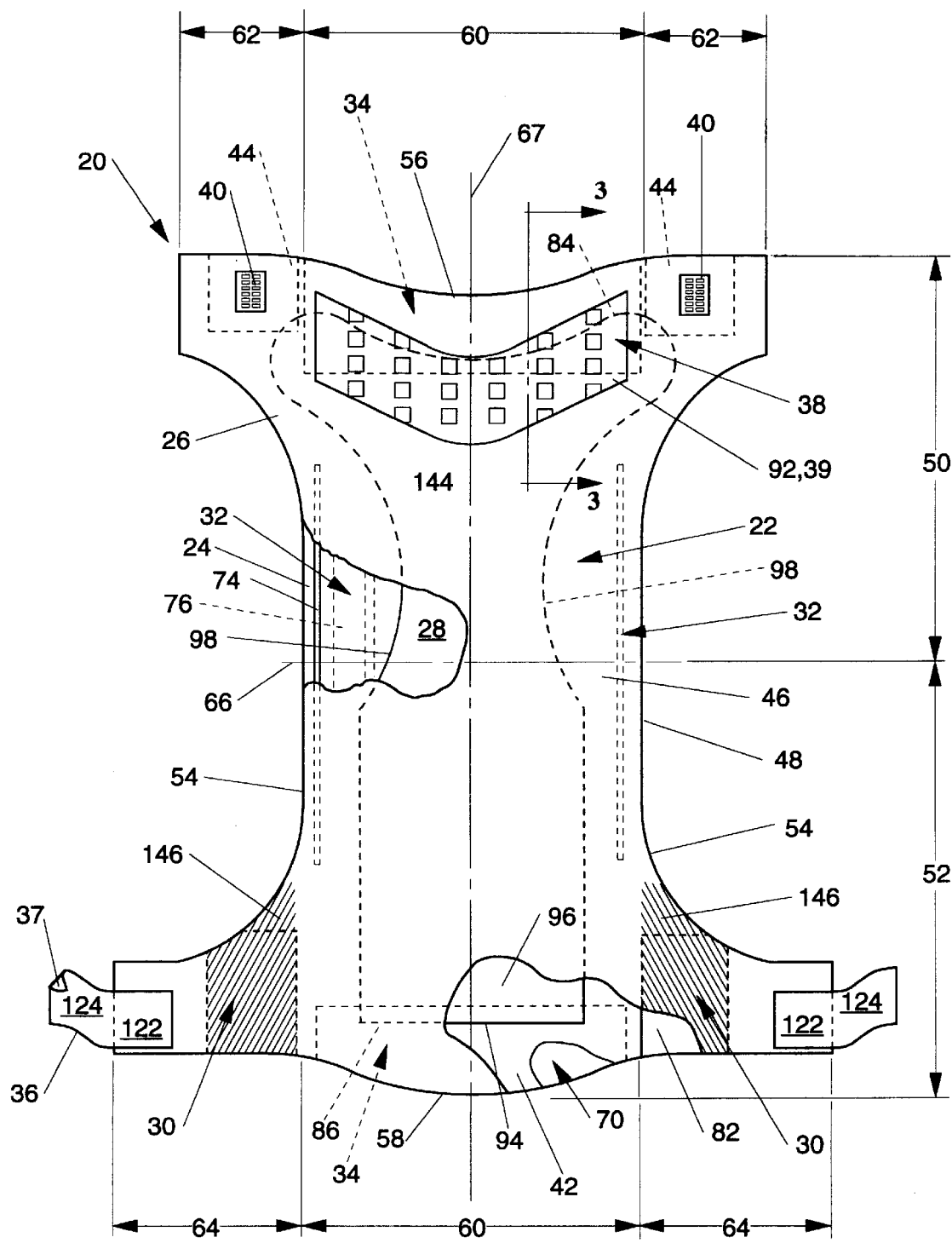
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out except in the side panels wherein the elastic is left in its relaxed condition) with portions of the structure being cut-away to more clearly show the construction of the diaper and with the portion of the diaper which faces away from the wearer, the outer surface, facing the viewer. As shown in FIG. 1, the diaper 20 comprises a containment assembly 22 preferably comprising an outer covering layer comprising a liquid pervious topsheet 24 and a liquid impervious backsheet 26 joined with the topsheet 24, and an absorbent core 28 associated with the outer covering layer, preferably being positioned between the topsheet 24 and the backsheet 26; elastic side panels 30; elastic leg cuffs 32; elastic waist features 34; and a closure system preferably comprising a dual tension fastening system. The dual tension fastening system preferably comprises a primary fastening system and a waist closure system. The primary fastening system preferably comprises a pair of securement members, preferably tape tabs 36, and a landing member 38. The waist closure system preferably comprises a pair of first attachment components 40 and a second attachment component 42. The diaper 20 also preferably comprises a positioning patch 44 located subjacent each first attachment component 40.

The containment assembly 22 is shown to have an outer surface 46 (facing the viewer in FIG. 1), an inner surface 48 opposed to the outer surface 46, a front waist region 50, a back waist region 52 opposed to the front waist region 50, and a periphery which is defined by the outer edges of the containment assembly in which the longitudinal edges are designated 54 and the end edges are designated front end edge 56 and back end edge 58. (While the skilled artisan will recognize that a diaper is usually described in terms of having a pair of waist regions and a crotch region between the waist regions; in this application, for simplicity of terminology, the diaper is described as having only waist regions, each of the waist regions including a portion of the diaper which would typically be designated as part of the crotch region). The inner surface 48 comprises that portion of the containment assembly 22 which is positioned adjacent to the wearer's body during use (i.e., the inner surface 48 generally is formed by at least a portion of the topsheet 24 and other components joined to the topsheet 24). The outer surface 46 comprises that portion of the containment assembly 22 which is positioned away from the wearer's body (i.e., the outer surface 46 generally is formed by at least a portion of the backsheet 26 and other components joined to the backsheet 26). The front waist region 50 and the back waist region 52 extend, respectively, from the front end edge 56 and the back end edge 58, respectively, to the lateral centerline 66. Each waist region comprises a central region 60 and a pair of side panels which typically comprise the outer lateral portions of the waist regions. The side panels positioned in the front waist region 50 are designated front side panels 62 while the side panels in the back waist region 52 are designated back side panels 64. (While it is not necessary that the pair of side panels or each side panel be identical, they are preferably mirror images of one of the other). In a preferred embodiment of the present invention, the back side panels 64 are rendered elastically extensible at an angle to the lateral direction as shown by the lines of activation in FIG. 1 to form elastic side panels 30. (The lateral direction (X-direction or width) is defined as the direction parallel to the lateral centerline 66; the longitudinal direction (Y-direction or length) being defined as the direction parallel to the longitudinal centerline 67; and the axial direction (Z-direction or thickness) being defined as the direction extending through the thickness of the diaper 20.)

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the containment assembly 22. The periphery defines the outer perimeter or, in other words, the edges of the containment assembly 22. The periphery comprises the longitudinal edges 54, the front end edge 56, and the back end edge 58.

Figure 2:
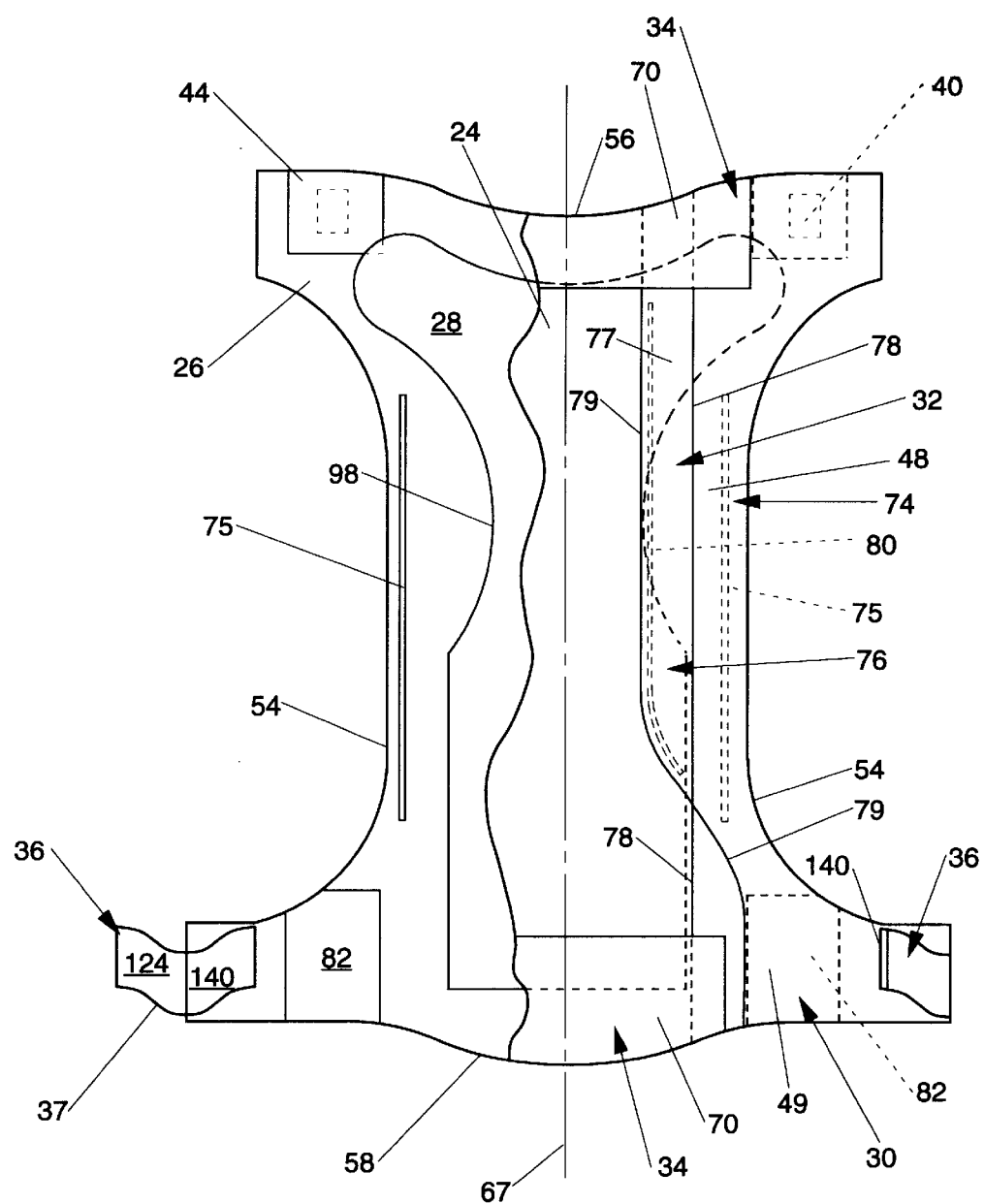
FIG. 2 is a plan view of the disposable diaper embodiment shown in FIG. 1 having portions cut-away with the inner surface of the diaper facing the viewer.

FIG. 2 shows a plan view of the diaper 20 with the inner surface 48 facing the viewer with portions of the topsheet 24 and the elastic leg cuffs 32 being cut away to more clearly show the construction of the diaper 20. As shown in FIG. 2, each elastic waist feature 34 preferably comprises an unitary waistcap/waistband 70 formed from a single piece of elastomeric material. The elastic leg cuff 32 comprises a gasketing cuff 74 and a barrier cuff 76. The barrier cuff 76 comprises a barrier flap 77 having a proximal edge 78 and a distal edge 79, and a spacing elastic member 80. The distal edge 79 is secured to the topsheet 24 laterally inward of the proximal edge 78 in the front waist region 50 and preferably laterally outward of the proximal edge 78 in the back waist region 52 such that the barrier cuff 76 is inflected to form a flipped out barrier cuff. The elastic side panels 30 each generally comprise the back side panel 64 and an elastic side panel member 82 operatively associated with the back side panel 64.

Figure 3:
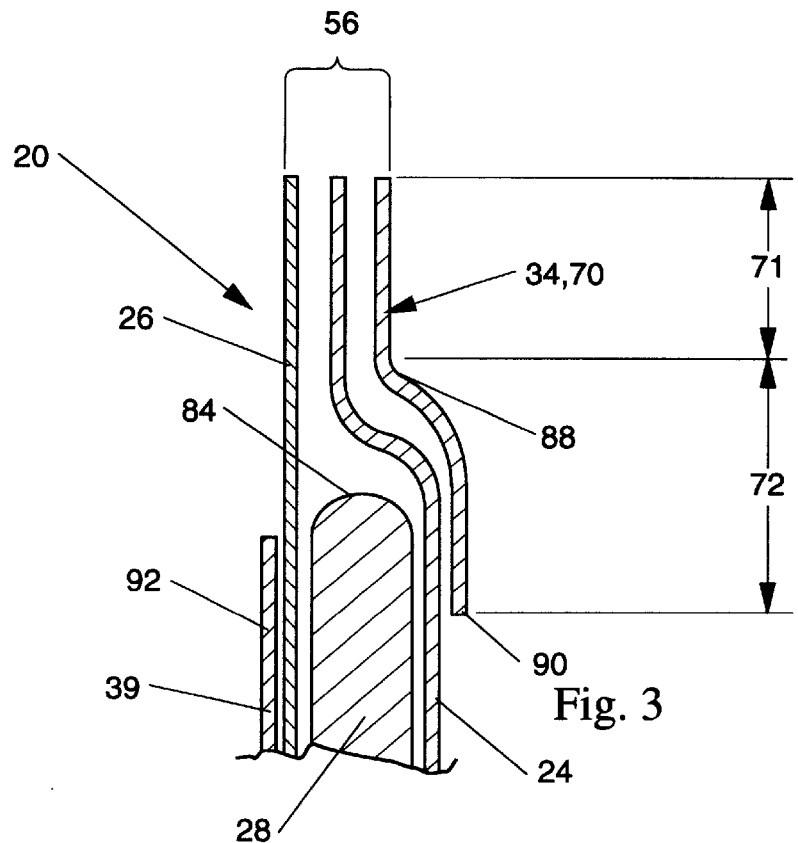
FIG. 3 is a fragmentary cross-sectional view of the disposable diaper embodiment of FIG. 1 taken through line 3—3 of FIG. 1 in the front waist region.

FIG. 3 is a cross-sectional view of the diaper 20 taken along section line 3—3 of FIG. 1 in the front waist region 50. The absorbent core 28 is disposed between the topsheet 24 and the backsheet 26, the topsheet 24 and the backsheet 26 extending beyond the front waist edge 84 of the absorbent core 28. The elastic waist feature 34 comprises a unitary waistcap/waistband 70 formed by a single piece of elastomeric material operatively associated with the topsheet 24. The unitary waistcap/waistband 70 has an elasticized waistband portion 71 and a waistcap portion 72. The elasticized waistband portion 71 is operatively associated in an elastically contractible condition adjacent the front end edge 56 by a waistband securement means (not shown) such as an adhesive as is known in the art so as to form an elasticized waistband. The waistcap portion 72 is contiguous with the waistband portion 71 and has a proximal edge 88 and a distal edge 90. The proximal edge 88 of the waistcap portion 72 is formed inboard of the front end edge 56, preferably between the front waist edge 84 of the absorbent core 28 and the front end edge 56, by joining a segment of the waistcap portion 72 to the topsheet 24 by attachment means (not shown) such as an adhesive bead so as to form a seal along the proximal edge 88. The distal edge 90 is disposed longitudinally inward of the proximal edge 88, and in the view shown, is not secured to any underlying elements of the diaper, particularly the topsheet 24, so that the waistcap portion 72 may be spaced away from the topsheet 24 so as to form a channel. The channel is open and able to restrain, contain, and hold body exudates within the diaper. A reinforcing strip 92 is secured to the backsheet 26 so as to form the landing member 38. The reinforcing strip 92 allows the first fastening component of the tape tab to releasably adhere to the second fastening component 39, the outer surface of the reinforcing strip, without tearing or puckering the reinforcing strip 92 or the backsheet 26. (Alternatively, the reinforcing strip could be positioned between the backsheet and the absorbent core to internally reinforce the landing member—the outer surface of the backsheet.)

The containment assembly 22 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly generally comprises the holder and the liner (i.e., the containment assembly comprises one or more layers of material to define the holder while the liner comprises an absorbent composite such as a topsheet, a backsheet, and an absorbent core.) For unitary absorbent articles, the containment assembly comprises the main structure of the diaper with other features added to form the composite diaper structure. Thus, the containment assembly 22 for the diaper 20 generally comprises the topsheet 24, the backsheet 26, and the absorbent core 28.

The topsheet 24 is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophobic material to isolate the wearer's skin from liquids contained in the absorbent core that is treated on at least one side with a surfactant to allow liquids to readily penetrate through its thickness.

In a preferred embodiment of the present invention, at least a portion of the topsheet is subjected to mechanical stretching in order to provide a "zero strain" stretch laminate that forms the elastic side panels. Thus, the topsheet is preferably elongatable, most preferably drawable, but not necessarily elastomeric, so that the topsheet will, upon mechanical stretching, be at least, to a degree, permanently elongated such that it will not fully return to its original configuration. In preferred embodiments, the topsheet can be subjected to mechanical stretching without undue rupturing or tearing of the topsheet. Thus, it is preferred that the topsheet have a low cross-machine direction (lateral direction) yield strength.

There are a number of manufacturing techniques which may be used to manufacture the topsheet. For example, the topsheet may be a nonwoven web of fibers. When the topsheet comprises a nonwoven web, the web may be spunbonded, carded, wet laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 in). Preferably, the topsheet has a basis weight from about 18 to about 25 g/m$^2$. A suitable topsheet is manufactured by Veratec, Inc., a division of International Paper Company, of Walpole, Mass., under the designation P-8.

The topsheet 24 is positioned adjacent the body surface 94 of the absorbent core 28 and is preferably joined thereto and to the backsheet 26 by attachment means (not shown) such as those well known in the art. Suitable attachment means are described below with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet and the backsheet are joined directly to each other in the diaper periphery and are indirectly joined together by directly joining them to the absorbent core by the attachment means (not shown). In an alternative embodiment, the absorbent core need not be joined to either the topsheet or the backsheet such that the absorbent core is allowed to "float" between them.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the diaper such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mils) to about 0.051 mm (2.0 mils).

In a preferred embodiment of the present invention, at least a portion of the backsheet is subjected to mechanical stretching in order to provide both a "zero strain" stretch laminate that forms the elastic side panels and, if desired, to prestrain the portion of the backsheet coinciding with the elastic waist feature or any other elastic feature. Thus, the backsheet is preferably elongatable, most preferably drawable, but not necessarily elastomeric, so that the backsheet will, upon mechanical stretching, be at least, to a degree, permanently elongated such that it will not fully return to its original undistorted configuration. In preferred embodiments, the backsheet can be subjected to mechanical stretching without undue rupturing or tearing. Thus, it is preferred that the backsheet have an ultimate elongation to break of at least about 400% to about 700% in the cross-machine direction as measured using a method consistent with ASTM D-638. Thus, preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designations X-8323, RR8220 blend for certain blown films, and RR5475 blend for certain cast films.

The backsheet 26 is preferably embossed (typically, to a caliper of about 0.127 mm (5.5 mils)) and/or matte finished to provide a more clothlike appearance. Further, the backsheet may permit vapors to escape from the absorbent core (i.e., breathable) while still preventing exudates from passing through the backsheet.

The backsheet 26 is positioned adjacent the garment surface 96 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waist-Containment Garment" which issued to Minetola and Tucker on Mar. 4, 1986. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The absorbent core 28 may be any absorbent means which is capable of absorbing and retaining liquids such as urine and other certain body exudates. As shown in the drawings, the absorbent core 28 has a body surface 94, a garment surface 96, side edges 98, a front waist edge 84, and a back waist edge 86.

The absorbent core 28 may be manufactured from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymer fibers or mixtures thereof including coform, chemically modified or cross-linked cellulosic fibers, tissue including tissue wraps and tissue laminates, absorbent foams, absorbent sponges, superabsorbent polymers, absorbent gelling materials, or any equivalent material or combination of materials. The configuration and construction of the absorbent core may also be varied (e.g., the absorbent core may have varying caliper zones, hydrophilic gradients, superabsorbent gradients, or lower average density and/or lower average basis weight acquisition zones; or may comprise one or more layers or structures). The total absorbent capacity of the absorbent core should, however, be compatible with the design loading and the intended use of the diaper. Further, the size and the absorbent capacity of the absorbent core may be varied to accommodate wearers ranging from infants through adults.

An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 4,834,735, entitled "High Density Absorbent Members Having Lower Density and Lower Basis Weight Acquisition Zones" issued to Alemany and Berg on May 30, 1989; and U.S. Pat. No. 5,147,345, entitled "High Efficiency Absorbent Articles For Incontinence Management" issued to Young, LaVon, and Taylor on Sep. 15, 1992; also describe absorbent structures that are useful in the present invention. A particularly preferred absorbent core is a dual layer structure having an acquisition core of chemically stiffened crosslinked cellulosic fibers and a storage core comprising a mixture of wood pulp fibers and superabsorbent particles such as disclosed in U.S. patent application Ser. No. 07/843,706, entitled "Absorbent Article With Elastic Waist Feature and Enhanced Absorbency", allowed, filed on Feb. 28, 1992, by Alemany and Clear, now U.S. Pat. No. 5,234,423. In these embodiments, the acquisition core may have any desired shape (it is preferably smaller in top surface area than the storage core) with the storage core having the preferred shapes as described herein.

Figure 6C:
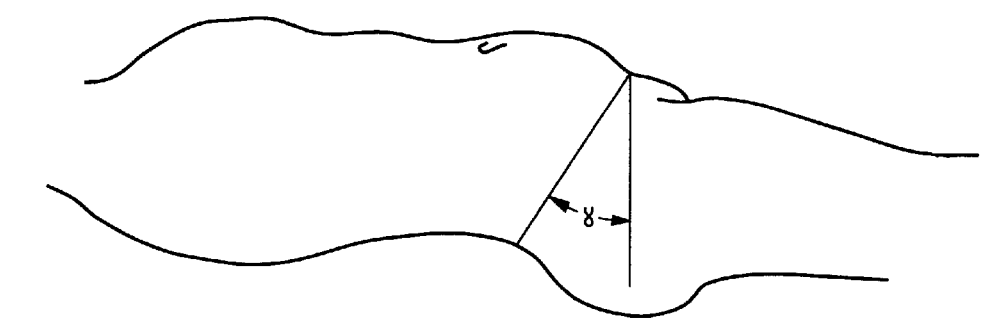
FIG. 6C is a side view of the body of a wearer showing the angle of the primary line of tension created by the present invention.
Figure 6B:
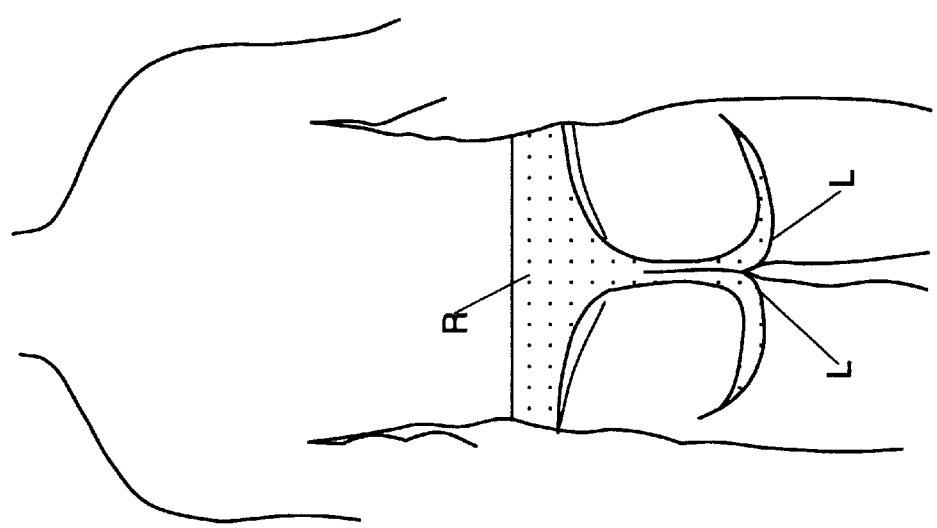
FIG. 6B is a back coronal view of the body of a wearer showing certain anatomical features and the location of the low motion zone.
Figure 6A:
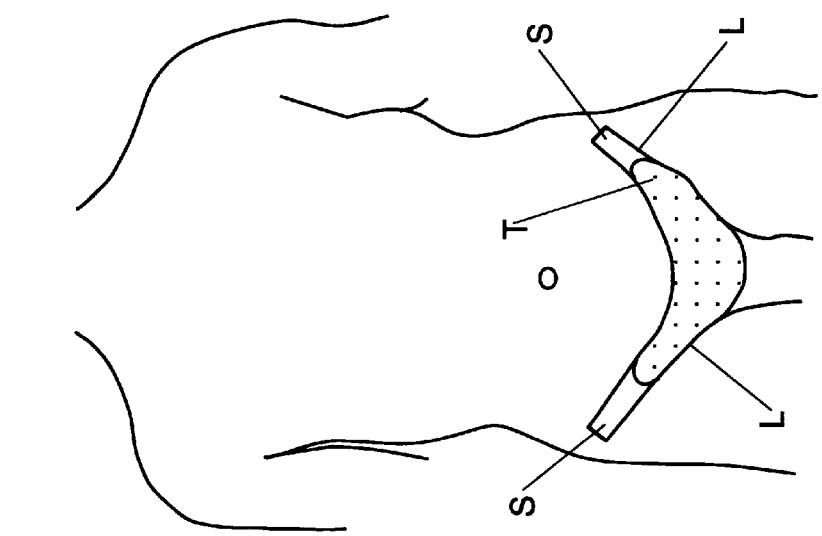
FIG. 6A is a front coronal view of the body of a wearer showing certain anatomical features and the location of the low motion zone.

FIGS. 6A and 6B show front and rear coronal views of a wearer showing where the low motion zone of the wearer is located. The low motion zone is delineated by the shaded zones in the drawings. As defined by the anatomy of the wearer, the "low motion zone" is defined to mean the zone or area of the body which despite dynamic movements remains substantially undeformed or undergoes very little motion. As shown in FIG. 6A, the low motion zone is bounded by the arcuate line in the hypogastric abdominal region connecting each anterior superior iliac spine, "S", through the crease or fold created by the rectus abdominus muscle, hereinafter the abdominal crease, "T". The abdominal crease is typically the fold or flexion crease of skin or muscle created by the abdomen when the wearer goes into a sitting position. The low motion zone is bounded on each lateral side by an arcuate line connecting the anterior superior iliac spine through the perineum along the inguinal ligament under the gluteus maximus (along the gluteal fold) to about the posterior inferior iliac spine, hereinafter the leg crease, "L". As shown in FIG. 6B, the low motion zone is bounded on the posterior of the wearer by the line connecting the posterior inferior iliac spine over the gluteous maximus and along the lumbar curve of the back, "R" (the small of the back). For purposes of the present invention, the low motion zone also includes the zone or area of the gluteous maximus (although not shaded in FIG. 6B) despite the fact that the gluteous maximus undergoes some dynamic motion since the forces generated in this zone caused by the wearer's movements tend to push up the absorbent core over the buttocks into the lumbar curve to enhance the fit of the absorbent core and the diaper rather than degrade such fit.

Figure 5:
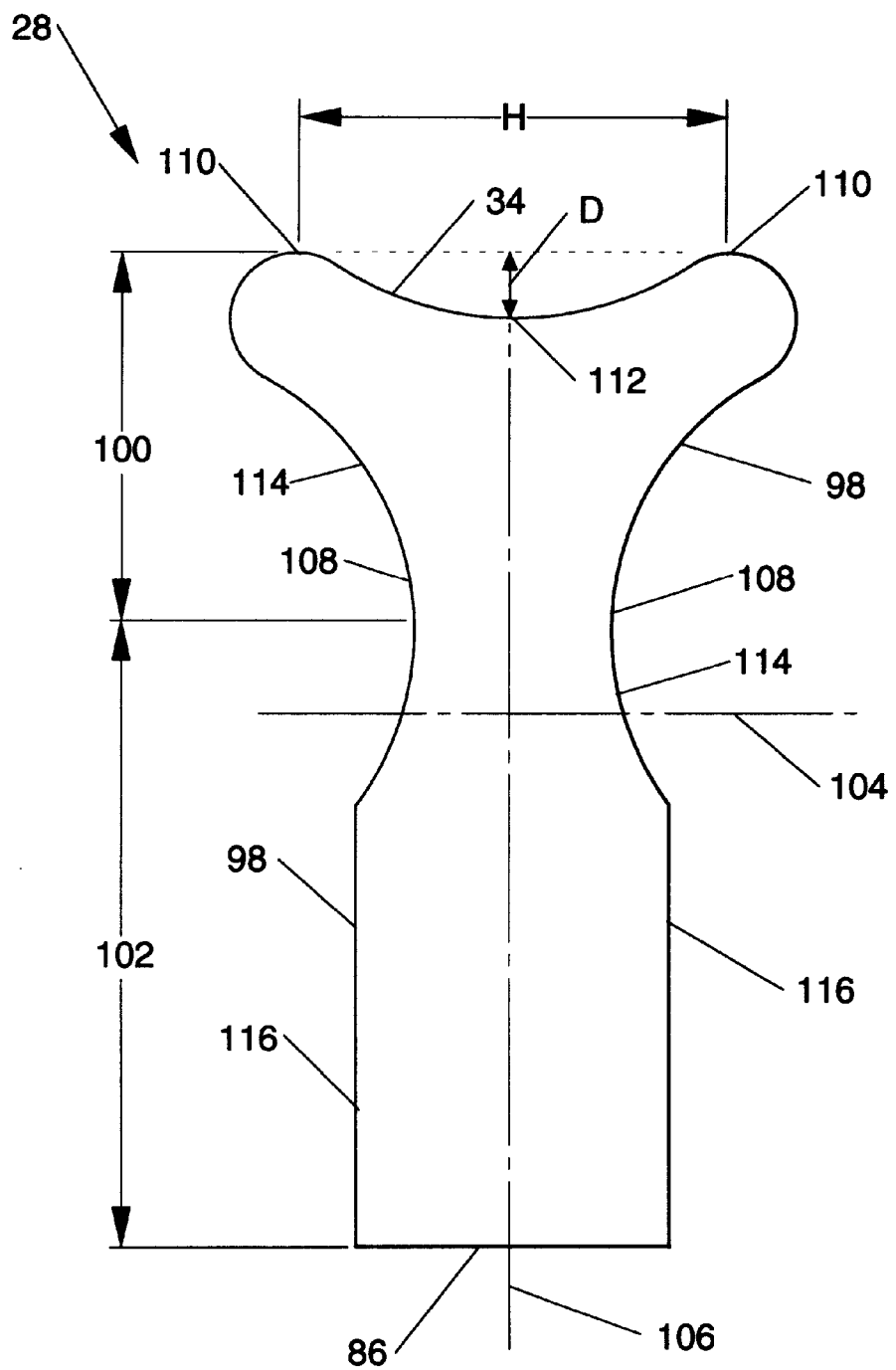
FIG. 5 is a plan view of the absorbent core shown in FIG. 1.

FIG. 5 shows a plan view of a preferred shape for the absorbent core 28 of the present invention. The shape of the absorbent core is designed so that the absorbent core fits substantially within the low movement, low distortion area (the low motion zone) of the anatomy of the wearer. This anatomically low motion zone-fitting absorbent core results in better fit, less distortion and movement of the absorbent core during wear, less bunching and roping of the core materials, and greater wearer comfort and mobility. Superior fit is achieved with this absorbent core design because the shape is matched to the wearer's anatomy so that there is less gapping, bunching and slumping of the absorbent core. Sustained dynamic fit is achieved because the absorbent core is designed to cover those parts of the wearer's anatomy that are subject to the least movement or change in shape during wear such that fit can be controlled from the initial fitting of the diaper on the wearer to taking the diaper off after being soiled. Further, because the absorbent core is designed to fit below or into the abdominal crease, the wearer's stomach has a reduced tendency to push the absorbent core down and cause the diaper to sag. Thus, the absorbent core remains substantially within the low motion zone of the wearer. Since the absorbent core is subjected to less dynamic forces caused by wearer movements because the absorbent core is within the low motion zone, the absorbent core also has less of a tendency to slump or rope. Wearer comfort and mobility is improved due to the decreased bulk of the absorbent core and the fact that the stiffer materials of the absorbent core are not positioned in zones subject to wearer movement.

The absorbent core 28 is shown in FIG. 5 to comprise a front section 100, a back section 102 contiguous with the front section 100, a front waist edge 84, a back waist edge 86, and side edges 98. The absorbent core 28 additionally has a lateral centerline designated 104 and a longitudinal centerline designated 106. The front section 100 and the back section 102 extend, respectively, from the front waist edge 84 and back waist edge 86 toward the lateral centerline 104 to the point corresponding to the centerpoint of the arcuate leg cut outs of the side edges 98, which is designated the crotch point 108.

As shown in FIG. 5, in order to securely fit below or at the abdominal crease of the wearer, the front waist edge 84 preferably has a substantially arcuate concave shape. As used herein, the term "arcuate" refers to lines other than a straight line although certain segments of the line may be straight line segments. The term "concave" is used to denote an arcuate line wherein the normals to the curve converge. The arcuate concave shape of the front waist edge 84 generally corresponds to the abdominal crease and is defined in an anatomical sense by three points on the front waist edge corresponding to three points on the wearer. The two points of the front waist edge 84 farthest away from the lateral centerline 104 adjacent the side edges 98 correspond to a point adjacent each anterior superior iliac spine of the wearer. Thus, these two points are designated "hip points" 110. The third point is the point along the longitudinal centerline 106 of the absorbent core 28 generally in line with the navel of the wearer typically defining the lower point on the abdominal crease of the wearer. This point is designated the "abdominal point" 112. It has been found that the hip points 110 and the abdominal point 112 have certain defined dimensions and relationships that do not vary significantly across wearers in comparable weight ranges. The hip points 110 are laterally spaced from another by a lateral distance, "H", less than or equal to about the lateral distance between the anterior superior iliac spines of the intended wearer. The abdominal point 112 is longitudinally spaced inward from the hip points 110 by a longitudinal distance, "D". It has been found that the ratio (H:D) of the lateral distance between the hip points 110, H, to the longitudinal distance between the hip points 110 and the abdominal point 112, D, should fall within a certain specified range in order for the front waist edge 84 to follow the abdominal crease of the wearer. The ratio H:D is preferably between about 6:1 and about 9:1, more preferably between about 7:1 and about 8:1. The distance between the hip points 110 can be easily selected based on targeted wearers and is preferably between about 14 cm and about 24 cm for wearers ranging from about 9 kgs to about 21 kgs. A table of ranges of hip point distances for given sizes of contemplated wearers is: birth–5 kgs: 6 cm–12 cm; 6 kgs–9 kgs: 11.4 cm–17.6 cm; 10 kgs–13 kgs: 14.5 cm–18.8 cm; 14 kgs–21 kgs: 16.8 cm–24 cm. While the curve connecting the hip points 110 and the abdominal point 112 can be any desired shape including straight line segments, it is preferred that the shape of the curve generally follow the curve of the abdominal crease. It has been found that the curve following the abdominal crease is generally an arc having a radius sufficient to fit the hip points 110 and the abdominal point 112. Using curve fitting techniques, a planar curve (rotated 29° into the x-y plane of the absorbent core) which has been found to approximate the arc of the abdominal crease is a polynomial curve having the equation: $y=1/(a+bx^2)$ wherein the coefficients a and b are preferably: a=0.45763285 and b=−0.021195617.

The shape of the side edges 98 of the absorbent core 28 are designed to provide a leg cut-out to fit at or within the leg creases of the low motion zone and a portion to preferably fit over the buttocks into the lumbar curve of the back. The side edges 98 thus each have a leg segment 114 and a buttocks segment 116.

The leg segment 114 has a substantially arcuate concave shape to fit within the leg creases. Along the arcuate curve forming the leg segment 114 is a point designated the "crotch point" 108 which corresponds to the narrowest portion of the absorbent core 28 in the leg segments 114. While the curve forming the leg segment 114, including the crotch point 108, can be any desired shape including straight line segments, it is preferred that the shape of the curve generally follow the curve of the leg crease. It has been found that the curve is generally an arc having a radius sufficient to fit the crotch point 108 through the leg creases. Using curve fitting techniques, a planar curve (rotated 31° into the x-y plane of the absorbent core) which has been found to approximate the arc of the leg crease is a polynomial curve having the equation: $y=a+bx+cx^2+dx^3+ex^4+fx^5+$ $gx^6$ wherein the coefficients a, b, c, d, e, f, and g are preferably: a=−0.02015642, b=0.02621513, c=0.055790377, d=−0.03472119, e=0.034448752, f=0.000858783, and g=−0.0022505.

In order to provide optimum fit of the absorbent core 28 in the low motion zone, the crotch points 108 are preferably positioned more toward the front of the absorbent core 28 such that the front section 100 is preferably shorter in longitudinal length than the back section 102. The front section 100 will thus fit low on the wearer to fit below or at the abdominal crease while the back section 102 preferably extends over the buttocks into the lumbar curve of the back. Therefore, the crotch points 108 are preferably positioned forward of the lateral centerline 104 of the absorbent core 28. The ratio of the longitudinal length of the back section 102 to the longitudinal length of the front section 100 is thus preferably greater than about 1:1.

The lateral width of the absorbent core 28 between the crotch points 108, the crotch width, can also be important in providing improved fit on the wearer. While the crotch width can vary widely, it is preferred that the crotch width be narrow enough to provide a comfortable fit on the wearer as well as optimal absorbency. It is preferred that the crotch width be small so that the absorbent core not bunch when the wearer's legs are closed. However, reducing the crotch width reduces the amount of absorbent material available in the zone of typical liquid deposition. If highly absorbent materials are used that provide sufficient capacity in this portion of the absorbent core, the crotch width can be greatly reduced so that the crotch width is small enough so that the absorbent core comfortably fits between the leg creases when the legs of the wearer are closed. Nevertheless, with most absorbent materials commonly used in diapers or other absorbent articles, the crotch width may need to be wider than the width of the wearer's body with the legs together so that the absorbent core will still have sufficient absorptive capacity. The shape of the leg segments, however, allow the side edges to conform to the low motion zone leg creases with minimal bunching and distortion. In alternative embodiments (and especially with stiffer absorbent materials), the absorbent core may be provided with means for providing enhanced bunching of the core material such as predisposed score lines, notches, or cut-outs of material. For the absorbent cores depicted in the drawings, it has been found that the crotch width should preferably be no greater than about 3 inches (7.5 cm), more preferably between about 1½ inches (3.78 cm) to 2½ inches (6.35 cm), most preferably about 2 inches (5 cm).

The buttocks segment 116 of the side edge 98 is contiguous with the leg segment 114 and comprises that portion of the side edge 98 extending from the leg segment 114 to the back waist edge 86. The buttocks segment 116 can be any desired shape. Preferably, the buttocks segment 116 is designed so that the buttocks segment 116 fits over the buttocks of the wearer into the lumbar curve of the back. In the preferred embodiment shown in FIG. 5, the buttocks segment 116 is essentially rectilinear (a straight line) and parallel to the longitudinal direction. The buttocks segment 116 is preferably rectilinear to allow wider elastic side panels in the back waist region.

The back waist edge 86 of the absorbent core 28 may also have a number of different shapes. For example, the back waist edge 86 may be arcuate or rectilinear or combinations of both. Further, recesses may be cut out of the back waist edge 86 to control bunching. In a preferred embodiment as is shown in FIG. 5, the back waist edge 86 is rectilinear and parallel to the lateral direction.

Thus, the absorbent core 28 has an overall modified T-shape that fits securely within the low motion zone of the wearer.

Figure 7A:
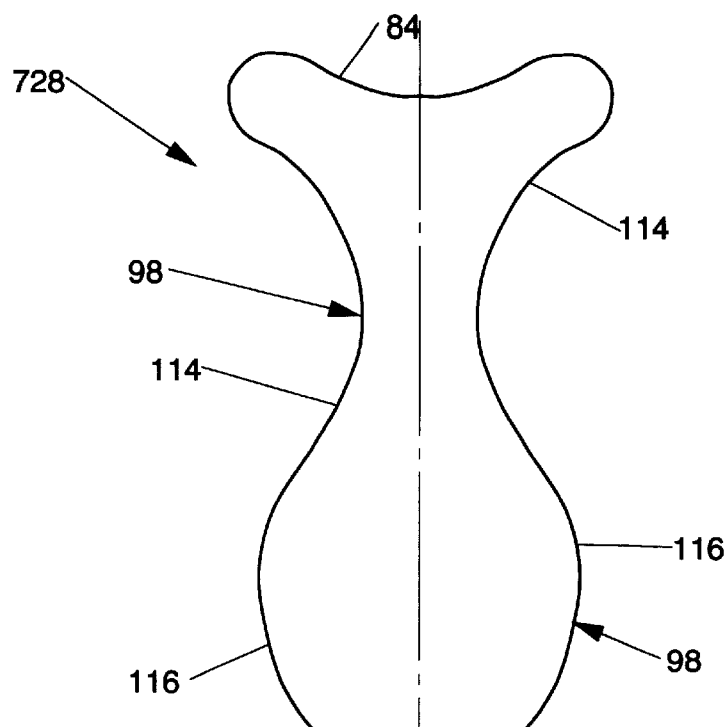
FIG. 7A is a plan view of an alternative embodiment of an absorbent core of the present invention.

FIG. 7A shows an alternative embodiment of an absorbent core of the present invention. The absorbent core 728 has an overall "whale" shape. The front waist edge 84 and the leg segments 114 are identical to the absorbent core depicted in FIG. 5. The buttocks segment 116 of the side edge 98 has a substantially arcuate convex shape to conform most closely about the buttocks. As used herein, the term "convex" denotes an arcuate line wherein the normals to the curve diverge. The back waist edge 86 has a substantially arcuate convex shape so that the absorbent core 728 fits conformably in the lumbar curve of the back of the wearer and so that the absorbent core shape enhances the formation of a primary line of tension directed at an angle on the wearer's body.

Figure 7B:
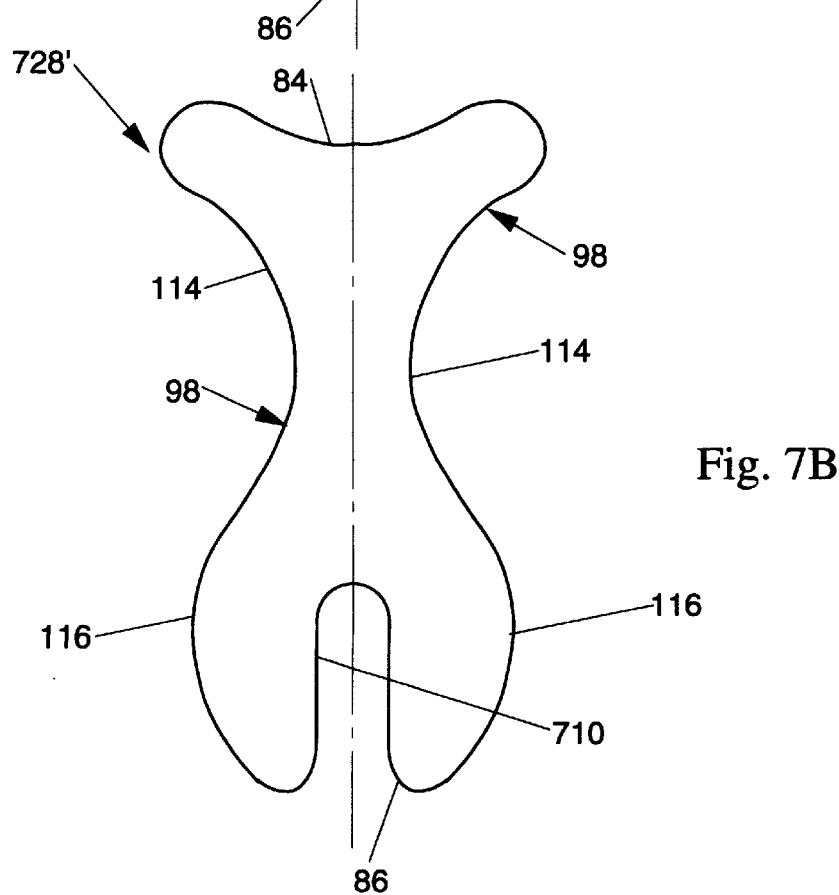
FIG. 7B is a plan view of a further alternative embodiment of an absorbent core of the present invention.

FIG. 7B shows a further alternative embodiment of an absorbent core of the present invention. The absorbent core 728' has a "modified whale" shape. The front waist edge 84 and side edges 98 are identical to the absorbent core depicted in FIG. 7A. The back waist edge 86 has a substantially arcuate convex shape having a recess 710 wherein the recess 710 is formed by a segment of the back waist edge 86 having an arcuate concave shape. This recess enhances containment of fecal matter deposited within the diaper.

Figure 7C:
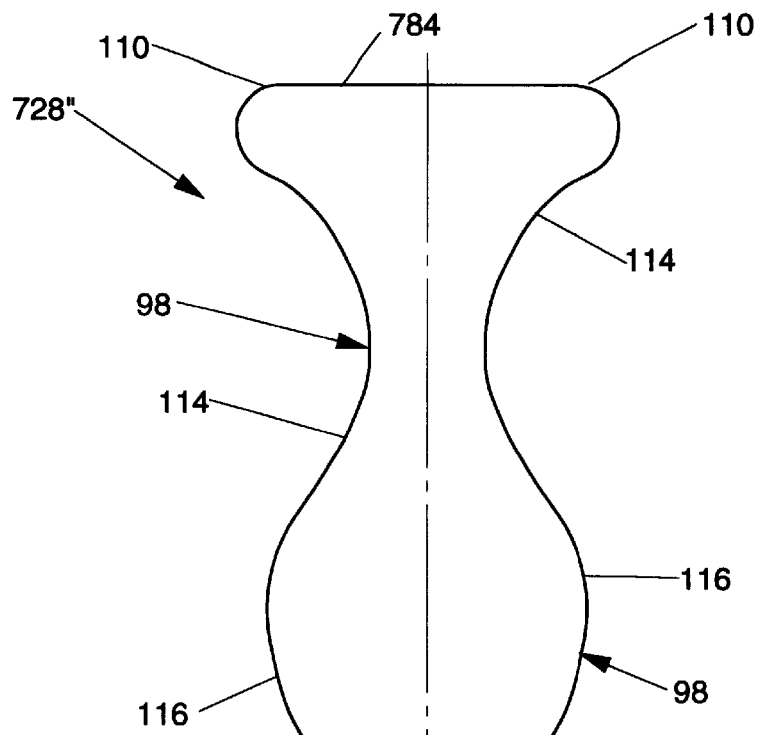
FIG. 7C is a plan view of a still further alternative embodiment of an absorbent core of the present invention.
Figure 9:
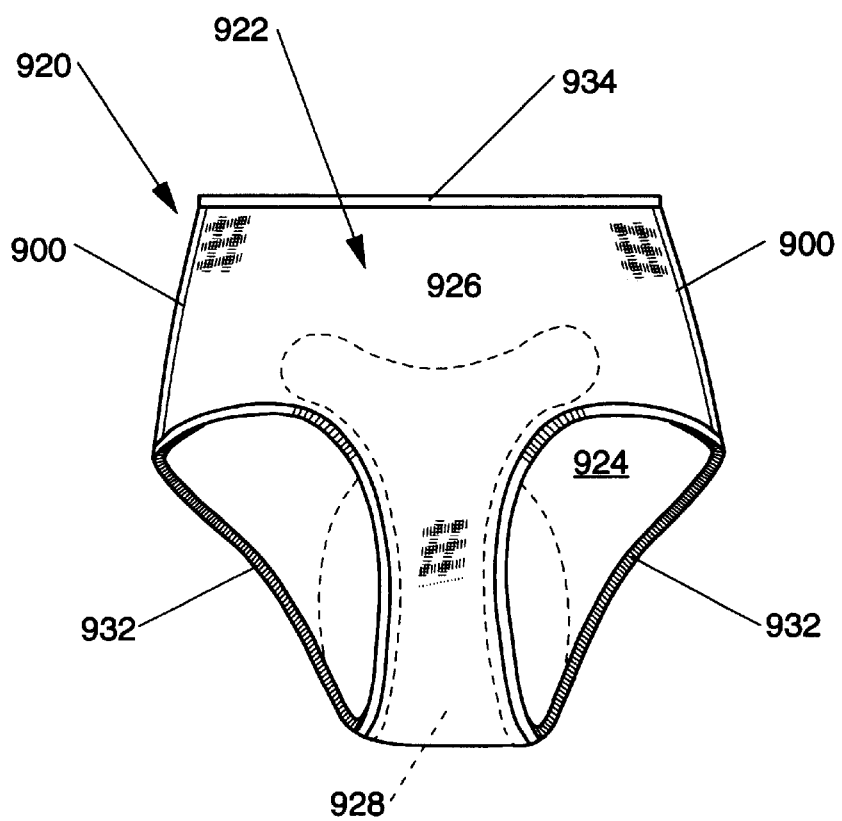
FIG. 9 is a front view of an alternative embodiment of an absorbent article of the present invention.

FIG. 7C shows a still further alternative embodiment of an absorbent core of the present invention. The absorbent core 728" has an overall "spade" shape. The front waist edge 784 has a rectilinear shape generally parallel to the lateral direction. The leg segments 114 are identical to the absorbent core shown in FIG. 5. Each buttocks segment 116 has an arcuate convex shape to conform most closely about the buttocks. The back waist edge 86 has an arcuate convex shape so that the absorbent core 728" fits conformably in the lumbar curve of the back and so that the absorbent core 728" enhances the formation of a primary line of tension directed at an angle on the wearer's body. The longitudinal distance between the hip points 110 of the front waist edge 784 is significantly shorter than the longitudinal distance between the hip points of the absorbent core shown in FIG. 7A. This shape for the absorbent core 728" provides improved fit with reduced core bunching, especially at the front and crotch of the absorbent core 728". The narrower crotch width and front waist edge help in preventing core bunching from the wearer's thigh movements. While the "spade" absorbent core 728" is useful in any of the containment assembly chassis shapes disclosed herein, it has been found that the spade absorbent core 728" is especially useful in an overall stretch chassis absorbent article such as is shown in FIG. 9.

Figure 7D:
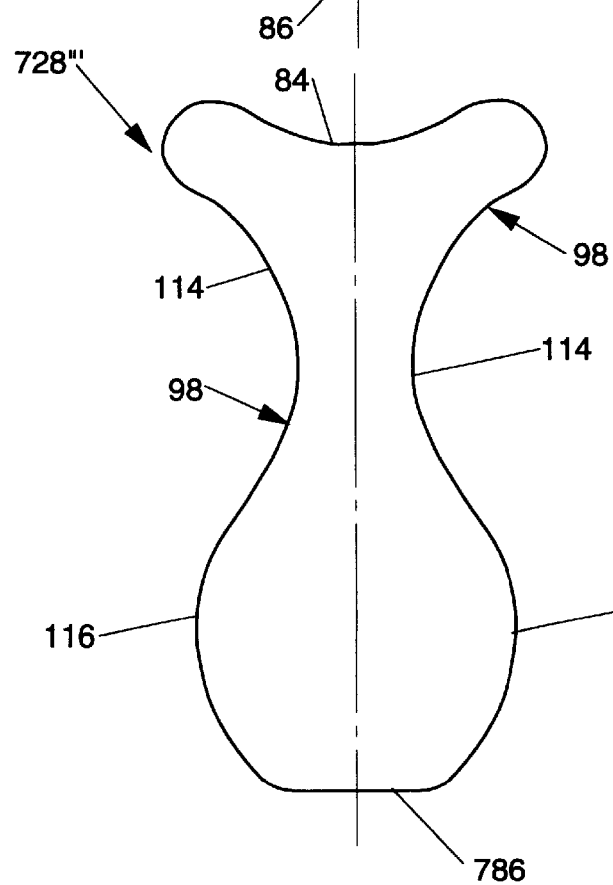
FIG. 7D is a plan view of an even still further alternative embodiment of an absorbent core of the present invention.

FIG. 7D shows an even still further alternative embodiment of an absorbent core of the present invention. The absorbent core 728''' has a "modified whale" shape. The shape of the absorbent core 728''' is similar to the whale absorbent core shown in FIG. 7A except that the back waist edge 86 has a rectilinear shape generally parallel to the lateral direction.

While the absorbent cores of the present invention may be positioned in a containment assembly having various sizes and shapes, it is preferred that the containment assembly also have certain shapes to better fit the absorbent core into the low motion zone of the wearer and reduce gapping of the containment assembly. Thus, as shown in FIG. 1, the containment assembly 22 preferably has a front end edge 56 having a substantially arcuate concave shape and a back end edge 58 having a substantially arcuate convex shape. The arcuate concave shape of the front end edge 56 allows the front end edge to be circumferentially disposed about the stomach of the wearer and can preferentially be disposed below the stomach so that the stomach will tend to not rub, abraid or otherwise press outwardly against the front end edge. In a particularly preferred embodiment, the stomach will overhang the primary line of tension so that hoop stresses against the diaper are controlled and sustained. The back end edge 58 preferably has an arcuate convex shape so that when the diaper is worn, the back end edge 58 is oriented diagonally downwardly across the hips toward the front of the wearer. Thus, the back waist region 52 is perched or otherwise supported through the small of the back so as to prevent the containment assembly 22 from interfering with the wearer's body during movements and to anchor the angled primary line of tension about the wearer from the lumbar curve of the back over the hips to under the abdominal crease. An arcuate convex shape for the back end edge 58 also tends to reduce gapping in the back waist region 52.

Figure 12:
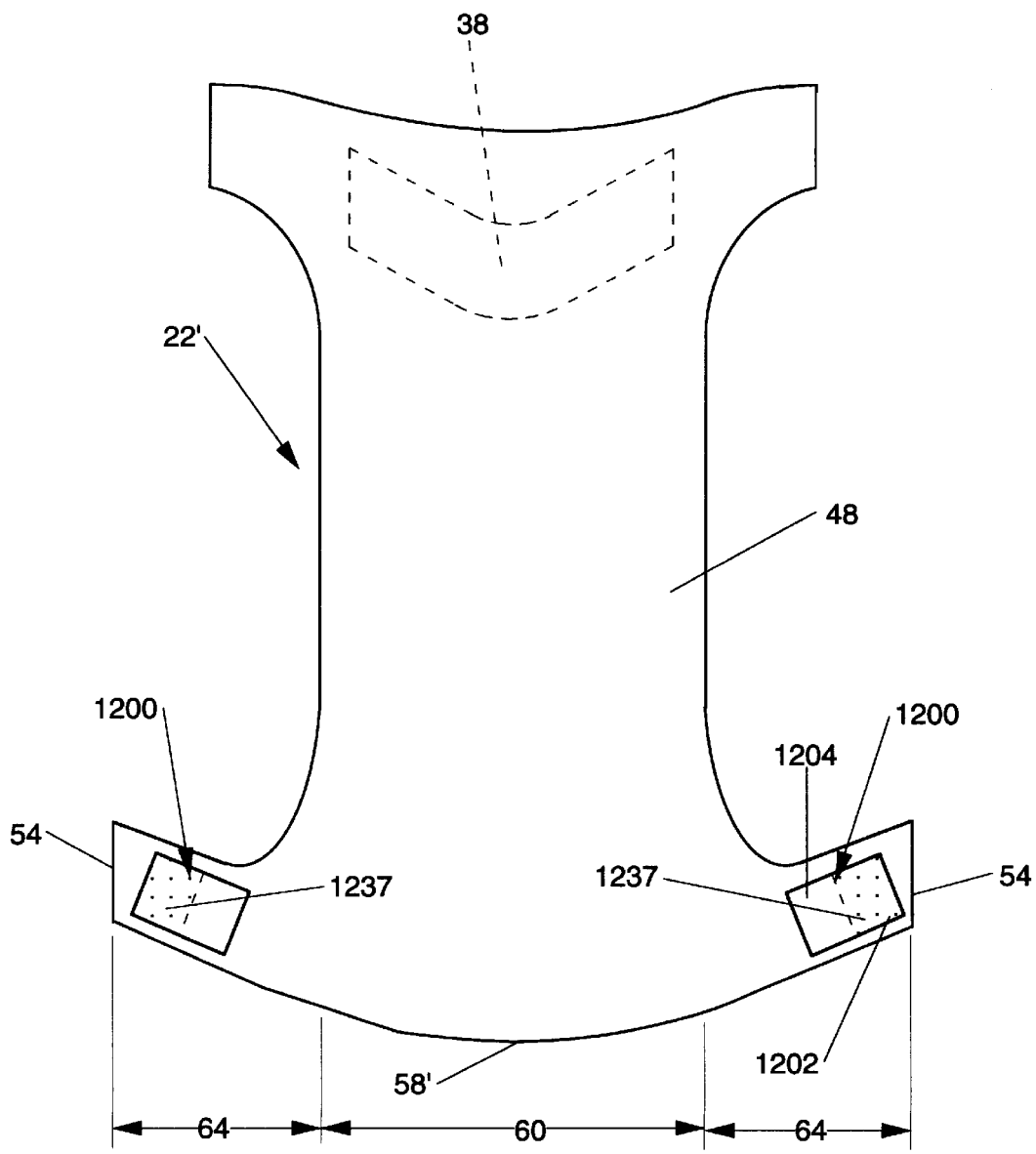
FIG. 12 is a simplified plan view of an alternative disposable diaper embodiment of the present invention showing an alternative shape for the containment assembly.

FIG. 12 shows an alternative embodiment of a containment assembly shape of the present invention wherein the back end edge 58' has a substantially arcuate convex shape with the curvature of the back end edge being continuous from one longitudinal edge 54 to the other longitudinal edge 54. Thus, not only the central region 60 of the containment assembly 22' has such an arcuate convex shape, but also the back side panels 64 have the same shape. This shape configuration for the back end edge enhances the formation of a continuous primary line of tension at an angle to the body of the wearer since the forces may resolved along the continuous curve of the back end edge. Further, this shape for the containment assembly 22' improves the application of the diaper and the initial fit since the back end edge 56' tends to follow the curve of the shape of the body of the wearer and the tape tabs naturally follow the angle of the landing member.

Figure 13:
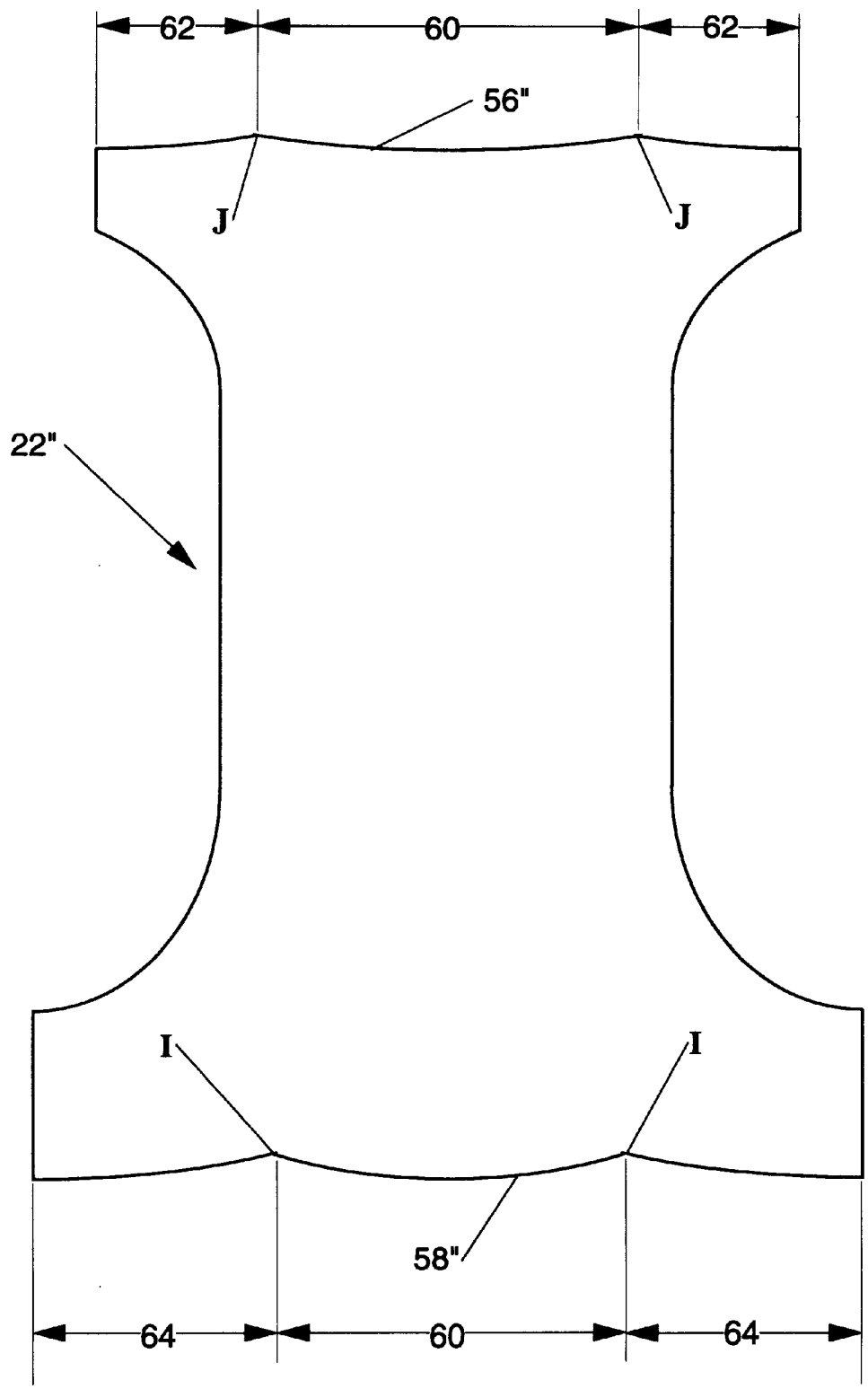
FIG. 13 is a simplified plan view of a still alternative disposable diaper embodiment of the present invention showing an alternative shape for the containment assembly.

FIG. 13 shows a further alternative embodiment of the present invention of a containment assembly shape wherein the back end edge 58" has an arcuate convex shape in the central region 60 and a separate arcuate convex shape in each back side panel 64. With this overall shape, two inflection points, "I", are defined in the back end edge 58" corresponding to the boundaries of the central region 60 with the back side panels 64. This overall shape of the back end edge 58" defines a "suspension bridge" shape. In addition, the front end edge 56" has a suspension bridge shape having an arcuate concave shape in the central region 60 and a separate arcuate concave shape in each front side panel 62 thereby defining two inflection points, "J". In a preferred embodiment of this containment assembly 22", the curvature of the central region 60 of the back end edge 58" matches the curvature of the central region 60 of the front end edge 56". More preferably, the curvature of the back side panels 64 matches the curvature of the front side panels 62. With this arrangement, it is easier to manufacture the diapers continuously on a high speed production line since the side panels can be inwardly folded and the diaper folded in half with only one cut needing to be made to form the arcuate end edges such that the single cut forms both the back end edge 58" of one diaper but also the front end edge 56" of the subsequent diaper. In addition, there is no wasted material and no scrap material that needs to be thrown away due to the single cut at the end edges such that the cost of the end product should be less. As will be recognized by those of skill in the art, there may be other shapes for the back end edge and the front end edge which allows such manufacturing ease.

Figure 4:
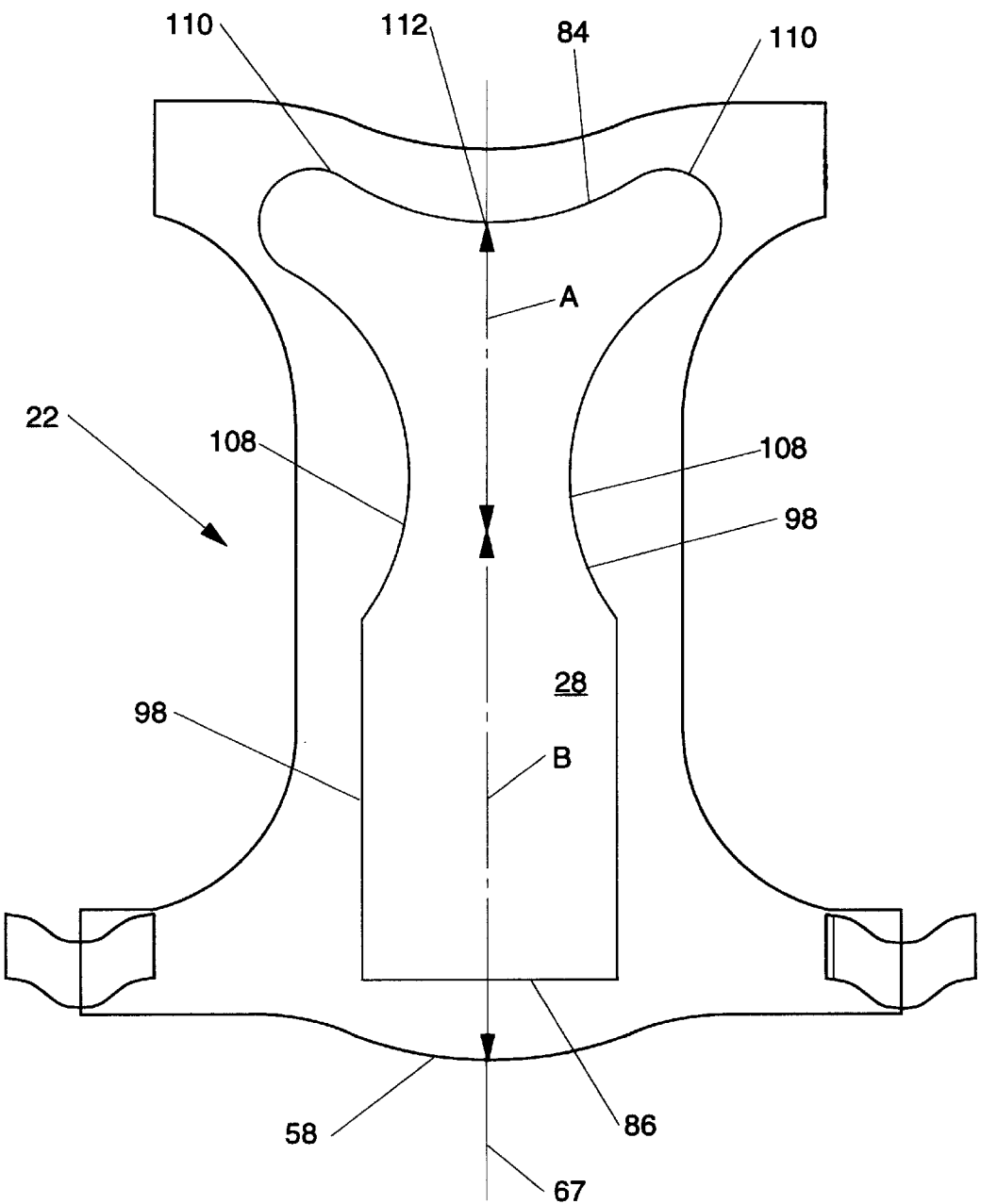
FIG. 4 is a simplified plan view of the disposable diaper embodiment shown in FIG. 1 showing the absorbent core in relation to the chassis (containment assembly) shape.

It has been found that there is a preferred relationship between the placement of the absorbent core 28 and the placement of the back end edge 58 of the containment assembly 22 to provide the preferred anchoring of the product about the wearer and the fit of the absorbent core in the low motion zone. As is shown in FIG. 4, this relationship is defined by two longitudinal distances on the containment assembly 22. The first distance is the longitudinal distance from the abdominal point 112 of the absorbent core 28 to the lateral line connecting the crotch points 108 of the side edges 98 of the absorbent core 28. This front length distance is designated "A". The second distance is the longitudinal distance between the lateral line connecting the crotch points 108 and a point on the back end edge 58 of the diaper on the longitudinal centerline 67. This back length distance is designated "B". It has been found that the ratio of the back length to the front length (B:A) is preferably greater than about 1.5:1, more preferably between about 2.0:1 and about 3.0:1, with a target for most diapers of about 2.5:1. This ratio between the back length, B, and the front length, A, allows the back end edge 58 to be positioned in the lumbar curve of the back and the front waist edge 84 of the absorbent core 28 to be positioned at or below the abdominal crease of the wearer. Thus, a line of tension (primary line of tension) can be developed around the wearer from the lumbar curve of the back over the hips to under the abdominal crease to anchor the product on the wearer. As shown in FIG. 6C, this ratio also defines an angle, α, between the line connecting the lumbar curve of the back and the navel, a lateral line with respect to the diaper, to a point below the abdominal crease of greater than about 5°, typically from 5° to about 60°, preferably from about 5° to about 30°, more preferably from about 10° to about 20°, most preferably about 15°. As discussed hereinafter, the closure system is designed to create a line or zone of tension causing a hoop force connecting the lumbar curve of the back over the hips to under the abdominal crease to form the anchoring function.

The diaper 20 is provided with a closure system (closure means) for anchoring the diaper about the wearer throughout the diapers use so the diaper has a reduced likelihood to sag/gap and slide/slip during use. The closure system provides a line or lines (zone) of tension (hereinafter, the primary line of tension) substantially about the perimeter of the low motion zone that imparts anchoring forces to maintain the position of the diaper throughout wearing. As shown in FIG. 6C, the primary line of tension is disposed at an angle, α, to the horizontal on the body of the wearer (an angle to the lateral direction of the diaper) such that the primary line of tension extends from around the lumbar curve of the back (the small of the back) over the iliac crest of the hips to below the line of the abdominal crease. Thus, the primary line of tension is disposed in the zone of minimal changing body dimension, a sustained wearing position (i.e., the primary line of tension is not disposed over the abdomen or the gluteous maximus which increase and decrease in dimension during movement), such that the primary line of tension stabilizes and maintains anchoring forces which maintain the position of the diaper on the wearer such that the diaper is unlikely to slide or slip downward during the entire time of use due to the movements of the wearer or to the force of the increased weight of the diaper when it is loaded. The angled primary line of tension created by the closure system also imparts an upward anchoring force on the diaper tending to pull the diaper up on the body, and thus counteract the weight force of the loaded diaper, since the primary line of tension has a vector component in the longitudinal direction. The normal anchoring forces created by the primary line of tension (another vector component of the angled primary line of tension) anchor the diaper, particularly the absorbent core, in the low motion zone since the normal anchoring forces act compressively to push the absorbent core toward the body. These normal anchoring forces thus assist in maintaining the fit of the diaper as well as reducing leakage since the absorbent core is maintained in close relationship with the body. The angled primary line of tension also tends to reduce redmarking since the anchoring forces are disposed in the low motion zone such that the body dimension is not increasing or decreasing along the primary line of tension which could cause red marking. In an especially preferred embodiment of the closure system of the present invention, the primary line of tension is continuous about the back and hips of the wearer to further enhance the magnitude of the anchoring forces. The overall design of the containment assembly 22, the elastic waist feature 34 in the back waist region 52 (the back waist feature), and the elastic side panels 30 (particularly the activation of the elastic side panels 30 at an angle) allow a continuous primary line of tension to be provided in the diaper.

Since the primary line of tension is to be disposed at an angle to the lateral direction to provide its anchoring function, the closure system is designed to provide an angled closure mechanism to insure such a primary line of tension is imparted to the diaper. The closure system may thus comprise a number of different fastening systems for providing an angled primary line of tension. For example, the closure system may simply comprise a primary fastening system. The closure system may additionally anchor a portion of the elastic waist feature in the front waist region, and, if desired, a portion of the elastic leg cuff. Thus, the closure system may comprise a full length fastener system. Examples of full length fastener systems are disclosed in U.S. Pat. No. 4,701,176 issued to Wilson, et al. on Oct. 20, 1987. Most preferably, as is shown in FIG. 1, the closure system comprises a dual tension fastening system designed to create the angled primary line of tension as described herein and to dynamically create/maintain tension, preferably another angled line of tension, through the elastic waist feature 34 in the front waist region 50 (hereinafter, front elastic waist feature) so that the front elastic waist feature also has sustained dynamic fit.

As shown in FIG. 1, the primary fastening system comprises a securement member, preferably tape tab 36, disposed adjacent each longitudinal edge 54 in the back waist region 52, and at least one landing member 38 disposed in the front waist region 50. Each securement member preferably comprises a tape tab 36 having a first fastening component 37. The landing member 38 comprises a complimentary second fastening component 39 engageable with the first fastening component 37. An exemplary primary fastening system wherein the first and second fastening components each comprise mechanical closure elements comprising hook and loop fastening materials is disclosed in U.S. Pat. No. 4,963,140 entitled "Mechanical Fastening Systems With Disposal Means For Disposable Absorbent Articles" issued to Robertson and Scripps on Oct. 16, 1990. A primary fastening system having combination adhesive/mechanical closure elements is described in U.S. Pat. No. 4,946,527 entitled "Pressure-Sensitive Adhesive Fastener and Method of Making Same" issued to Battrell on Aug. 7, 1990. In a preferred embodiment of the present invention as is shown in FIG. 1, the primary fastening system comprises an adhesive tape tab fastening system comprising a tape tab 36 having a first fastening component 37 comprising an adhesive attachment layer, and a landing member 38 having a second fastening component 39 comprising a reinforcing strip 92 joined to the backsheet 26. Examples of such adhesive tape fastening systems are disclosed in U.S. Pat. No. 3,848,594 entitled "Tape Fastening System For Disposable Diaper" issued to Buell on Nov. 19, 1974; and the adhesive tape tabs, reinforcing strip, and indicia means disclosed in U.S. Pat. No. 4,662,875 entitled "Absorbent Article" issued to Hirotsu and Robertson on May 5, 1987.

Each securement member of the primary fastening system is intended to provide a fastening means for engaging the landing member so as to provide a secure, preferably a variable positioning, side closure for the diaper that anchors the absorbent core in the low motion zone of the wearer. Thus, the securement member comprises a fastening component. Each securement member also preferably comprises a means for positioning the fastening component adjacent the landing member so as to achieve the side closure. Thus, the securement member may comprise any of the well known configurations and means for achieving a side closure on a diaper such as (i) a patch or strip of a fastening component disposed to form a portion of the inner surface of the diaper, an inner fastening member (e.g., U.S. Pat. No. 4,610,682 issued to Kopp on Sep. 9, 1986; and U.S. Pat. No. 3,141,161 issued to Farris on Jul. 21, 1964) or (ii) a tape tab having a fastening component positioned thereon.

As shown in FIG. 1, each securement member preferably comprises a tape tab 36. The tape tabs 36 must be able to be secured to the landing member 38 so as to provide a primary line of tension through the diaper at an angle to the lateral direction. Thus, the tape tab 36 is generally shaped and oriented to allow the first fastening component 37 to engage the second fastening component 39 of the landing member 38 so as to provide a primary line of tension at an angle to the lateral direction, preferably through the diaper substantially about the low motion zone.

Figure 8:
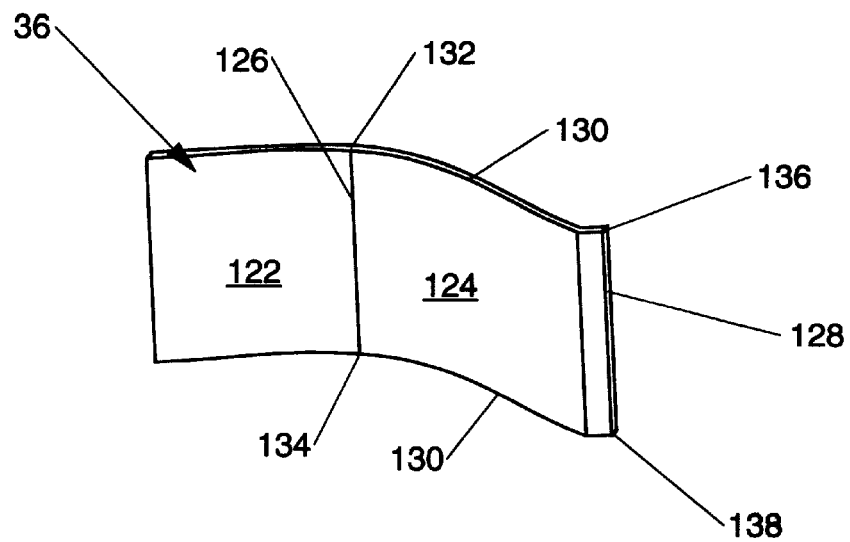
FIG. 8 is a plan view of a preferred tape tab useful in the present invention.

FIGS. 1 and 8 shows a preferred embodiment of a preferred tape tab 36 of the present invention. The tape tab 36 is joined to the backsheet 26 to create a fixed portion 122 (i.e., that end of the tape tab joined to the diaper 20 during manufacture). The tape tab 36 has another element which is the tab portion 124 (i.e., that end of the tape tab contiguous to the fixed portion 122 that is disposed so as to be capable of extending laterally outwardly beyond the longitudinal edge 54 and that is grasped by the diaperer in securing the diaper 20 on the wearer). The tab portion 124 has a proximal edge 126 contiguous to the fixed portion 122, a distal edge 128, and sidelong edges 130. The proximal edge 126 has a top point 132 and a bottom point 134. The distal edge 128 has an upper point 136 and a lower point 138. In preferred embodiments of tape tabs of the present invention, the tab portion 124 is shaped and oriented at an angle to the lateral direction to insure the formation of the primary line of tension at an angle to the lateral direction. Thus, the upper point 136 of the distal edge 128 is disposed at an angle to the lateral direction from the top point 132 of the proximal edge 126, and preferably the bottom point 134 of the distal edge 128 is disposed at an angle (not necessarily the same angle) to the lateral direction from the bottom point 134 of the proximal edge 126. In the embodiment shown in FIG. 8, the sidelong edges 130 are curved to allow angled taping in order to follow the diaper shape/build of the wearer, to create the angled primary line of tension about the low motion zone to anchor the diaper on the wearer, and to allow the diaperer to conveniently apply the tab portion 124 on the landing member 38 so as to accommodate the diaper design. Further, the curved shape of the sidelong edges 130 of the tab portion 124 allows high tape placement in the back waist region 52 yet allows low tape placement on the landing member 38 to minimize marking of the stomach, hips and legs of the wearer to improve the comfort of the diaper for the wearer. The tab portion 124 also accommodates the leg of the wearer in that if the tape tab was positioned too low on the product, marking could occur on the legs of the wearer which would negatively impact comfort and fit.

It has been found that the angle formed between the proximal edge 126 of the tab portion 124 and the distal edge 128 of the tab portion 124 should be less than about 30°, preferably between about 5° and about 30°, more preferably between about 10° and about 25°, most preferably about 20°, to approximate the angle of fit of the diaper on the wearer. A tab portion 124 having an angle greater than about 30° tends to cause the primary line of tension to be very narrow through the tape tab which may result in tape rotation or product rotation due to the non-resolved forces set up in the tape tab. The tape tab would also not follow the angle of the product to set up the angled primary line of tension of approximately 15°.

In a preferred embodiment of the tape tab 36 as shown in FIG. 8, the fixed portion 122 is between about 28 mm and about 30 mm long in the lateral dimension, the tab portion 124 is about 35 mm (1.375 in) long in the lateral direction, and the overall width of the tape tab in the longitudinal direction is about 29 mm (1.125 in). The angle between the proximal edge top point 132 and bottom point 134 and the distal edge upper point 136 and lower point 138, respectively, of the tab portion 124 is about 20° so that the longitudinal distance between the top point 132 or the bottom point 134 of the proximal edge 126 and the upper point 136 or lower point 138 of the distal edge 128 is about 13 mm (0.5 in). (The distal edge 128 of the tab portion 124 may also be provided with rounded corners to eliminate the possibility of harsh corner edges contacting the wearer's skin so as to prevent stomach and leg red marking.)

As shown in FIG. 2, the preferred tape tab 36 also comprises a release portion 140 joined to the topsheet 24. The release portion 140 allows the tab portion 124 to be inwardly folded during manufacture to protect the first fastening component 37 (adhesive attachment layer) from contamination or delamination 30 prior to use. The tab portion 124 is preferably shorter in the lateral direction than the release portion 140, preferably about 3 mm (⅛ in) in a preferred embodiment as shown in FIG. 2, so that it is easier for the diaperer to initially grasp the tab portion 124. (Alternatively, the tab portion 124 may be longer in the lateral direction so that the grip tab on the distal edge 128 of the tab portion 124 extends beyond the release portion 140.) The release portion 140 extends inwardly from the longitudinal edge 54, in certain embodiments preferably up to and juxtaposed over a portion of the elastic side panel member 82 so that the load carried by the tape tab 36 is transferred into the elastic side panel member 82 resulting in more effective distribution of the anchoring forces created by the closure system.

In alternative preferred embodiments of the present invention, the tab portion 124 or the entire tape tab may be applied to the containment assembly 22 at an angle to the lateral direction to provide the angled primary tension line desired. For example, a rectangular tape tab such as is known in the art or a tape tab having any other shape may be rotated with respect to the lateral direction when applied to the containment assembly such that the tape tab is disposed at an angle to the lateral direction of preferably between about 5° to about 30°, preferably from about 15° to about 20°, to provide an angled primary line of tension. While such a tape tab will adequately work with many embodiments of the present invention, it is not as preferred as the tape tab 36 shown in FIG. 8.

The flexibility of the materials making up the various portions of the tape tab has also been found to be important in avoiding skin marking of the legs and waist of the wearer. Stiff tape tabs have a tendency to mark the skin since they are not flexible enough to bend or flex when the wearer moves and generates forces against the tape tab. The flexibility of the tape tabs is an especially important design parameter for the tape tabs of the present invention due to the high tension created in the diaper along the side panels because of the elastic side panels 30 and the fit provided by the diaper 20. Thus, in an especially preferred embodiment of the present invention, at least the tab portion 124, and preferably the fixed portion 122 and the release portion 140 are manufactured from materials which are extremely flexible. While the flexibility of the tape tab materials can be measured in a number of ways, it has been found that there is a preferred test method for measuring the flexibility of the tape tab materials. Using a Flexural Bending Test, as defined hereinafter, each of the various portions of the tape tabs, particularly the tab portion 124, should have a Bending Flexure Extension Force of less than about 50 grams$f$, preferably less than about 30 grams$f$, more preferably less than about 20 grams$f$.

Preferred materials for the tape tab comprise a polymeric material, preferably a polyethylene film. Tape materials suitable for use as the tape tabs are XPF-3062, XPF-3-014, Y-9376, or Y-9030 as are available from the Minnesota Mining and Manufacturing Company of St. Paul, Minn. Preferred tape tabs including a pressure-sensitive adhesive for the first fastening component are available from the Minnesota Mining and Manufacturing Company under the code number XPF-3062. A preferred release portion include that available from Minnesota Mining and Manufacturing Company under the code number KS-0076.

FIG. 12 shows an alternative embodiment of a securement member of the present invention. The securement member comprises an inner fastening member 1200 positioned on the inner surface 48 of the back side panels 64. The inner fastening member 1200 has a securement portion 1202 and a release portion 1204. The securement portion 1202 has a first fastening component 1237 preferably comprising a layer of adhesive disposed on it to form the side closure of the diaper. The release portion 1204 serves to protect the first fastening component 1237 from contamination prior to use of the diaper. The securement portion 1202 is preferably folded over onto the release portion 1204 during manufacture such that the user would release the securement portion 1202 from the release portion 1204 prior to use. The securement portion 1202 need not be joined to the back side panel 64 such that only the securement portion 1202 need be folded over or the securement portion may be secured to the back side panel such that the back side panel along with the securement portion need to be folded over onto the release portion 1204. As shown in FIG. 12, the securement member 1202 is positioned laterally outwardly from the release portion 1204; however, the position of each may be reversed, if desired. FIG. 12 also shows that the inner fastening member 1200 has a generally rectangular shape and is disposed at an angle to the lateral direction to enhance the formation of the angled primary line of tension. Alternatively, the inner fastening member may have any other shape, including the shape of the tab portion and release portion of the tape tab shown in FIG. 1 and FIG. 8.

The inner fastening member 1200 may alternatively not be disposed at an angle, while the first fastening component 1237 may form such an angle.

In an alternative embodiment of the tape tabs described herein, the fixed portion and the release portion may comprise the same element such as that shown in FIG. 12 except that the tab portion extends laterally outwardly from the longitudinal edge. Thus, the fixed portion is secured to the inner surface of the containment assembly and coated on its exposed surface with a release coating such that the tab portion may be laterally inwardly folded by the manufacturer to protect the first fastening component. The advantage of such a construction for the tape tabs of the present invention is that only one layer of tape tab material is joined to the containment assembly in the portion of the back side panel containing a portion of the tape tab such that the flexibility of this portion of the back side panel is enhanced to thereby reduce the possibility of skin marking of the wearer.

The first fastening component 37 of the securement member forms the closure between the securement member and the complementary second fastening component 39 of the landing member 38. Thus, the first fastening component 37 provides a means for engaging the complementary second fastening component 39 of the landing member 38 to maintain the first waist region 56 and the second waist region 58 in an overlapping configuration to provide a secure side closure for the diaper 20. Further, it is preferred that a diaper fit a range of different size wearers and that the fastening system be simple and easy to use. Therefore, the fastening components should allow for variable positioning of the zone of closure so that the diaper may fit a range of sizes of wearers while also being simple to fasten with minimal effort. The fastening components thus preferably comprise any of the well known attachment means for achieving an adjustable positioning closure as defined hereinafter. Examples of such adjustable positioning attachment means include an adhesive attachment layer such as pressure-sensitive adhesives as are known in the art, mechanical closure elements such as hook fastening materials or loop fastening materials, cohesive materials as are known in the art, or a combination of adhesive/mechanical closure elements, each as hereinafter described with respect to the waist closure system.

The first fastening component 37 is disposed on the securement member such that it may be a separate member joined to and associated with the securement member or a unitary member with the securement member. For example, the topsheet 24 or the backsheet 26 may be manufactured from a material that mechanically engages the landing member 38 (the topsheet 24 or the backsheet 26 being a unitary fastening component). Alternatively, a discrete patch or strip of material may be joined to the securement member (a separate fastening component). Preferably, the first fastening component 37 is a separate material, such as an adhesive attachment layer or a mechanical closure element, positioned on and joined to the tape tab 36. The first fastening component 37 preferably comprises an adhesive attachment layer coated on the tab portion 124 to form the fastening surface of the tape tab 36.

In addition, the first fastening component 37 may be positioned anywhere on the securement member. For example, the first fastening component 37 may be positioned in the back side panels 64 adjacent the longitudinal edges 54. (Exemplary examples of this construction are shown in U.S. Pat. No. 4,610,682 issued to Kopp on Sep. 9, 1986; and in U.S. Pat. No. 3,141,161 issued to Farris on Jul. 21, 1964; and FIG. 12.) When the securement member comprises a tape tab, the first fastening component 37 is preferably positioned either on all or at least a portion of the tab portion 124. The first fastening component 37 may comprise a combination adhesive/mechanical closure element having an adhesive attachment layer and a mechanical closure element disposed on another area of the tab portion 124. An exemplary embodiment of this configuration is disclosed in the hereinbefore referenced U.S. Pat. No. 4,963,140 issued to Robertson on Oct. 16, 1990.

The landing member 38 of the primary fastening system provides a means for securing itself to the securement member to provide a side closure and to maintain the front waist region 50 and the back waist region 52 in an overlapping configuration. The landing member 38 may be disposed anywhere on the diaper 20 so long as it can engage the securement member so as to provide the side closure and, preferably a variable positioning side closure. For example, the landing member 38 may be disposed in the back waist region 52, in the front waist region 50, or in any region or zone or on any element of the diaper 20, which is disposed to engage the securement member 42. Because the landing member 38 determines the location of where the securement member 42 should be placed for optimum fit, the landing member 38 is preferably designed so as to allow variable positioning of the side closure so that the diaper may fit a range of sizes, so that an overlap between the front waist region 50 and the back waist region 52 is achieved, so that an angled primary line(s) of tension is established through the diaper to anchor it on the wearer, and preferably so that when the side closure is formed the attachment components of the waist closure system engage each other such that the formation of the side closure also passively forms the waist closure.

The landing member 38 can assume varying sizes and shapes. In a preferred embodiment of the diaper 20 as illustrated in FIG. 1, the landing member 38 comprises a reinforcing strip 92 having a modified chevron shape so as to create the angled primary line of tension of the present invention.

The landing member 38 comprises a fastening component (second fastening component 39) engageable with the fastening component of the securement member (first fastening component 37). Thus, the fastening component of the landing member 38 (second fastening component 39) may be manufactured from a wide range of materials and configurations capable of securely engaging the fastening component of the securement member (first fastening component 37). The second fastening component 39 may either be a discrete, separate element or elements joined to the diaper 20 and/or a unitary piece of material with an element of the diaper 20. The second fastening component 39 may thus comprise, for example, a portion of the backsheet 26. As shown in FIG. 1, the second fastening component 39 preferably comprises a reinforcing strip 92 joined to the external surface of the backsheet 26 in the front waist region 50. The second fastening component 39 is secured to the backsheet 26 preferably by an adhesive attachment means (not shown) as have been herein discussed. (In an alternative embodiment of the present invention, the second fastening component comprises a portion of the backsheet with a reinforcing strip(s) secured to the internal surface of the backsheet (i.e., an internal reinforcement system).)

When the first fastening component 37 comprises a mechanical closure element, the second fastening component 39 also comprises a mechanical closure element. Thus, when the first fastening component 37 comprises a hook fastening material, the second fastening component 39 preferably comprises a loop fastening material. When the first fastening component 37 comprises an adhesive attachment layer, the second fastening component 39 of the landing member 38 preferably comprises a reinforcing strip 92 and/or the backsheet 26. In a preferred embodiment of the present invention as shown in FIG. 1, the second fastening component 39 preferably comprises a reinforcing strip 92 releasably engageable with the adhesive attachment layer of the tape tabs 36. The reinforcing strip 92 may comprise any of a number of materials. The reinforcing strip 92 preferably comprises a sheet of biaxially oriented polypropylene film.

The reinforcing strip 92 is also preferably provided with indicia means 144 for aiding the diaperer in fitting the diaper to a wearer to obtain optimal waist fit and leg opening fit. The indicia means 144 may be any type of lines, patterns, ornamental designs, symbols, script, color codes, or other markings which have the capability, either inherently or with additional denotation, to aid an individual fitting the diaper to the wearer to promptly locate the desired affixation points for a particular tape tab fastener. Such indicia means 144 are more fully described in U.S. Pat. No. 4,662,875 entitled "Absorbent Article" which issued to Hirotsu and Robertson on May 5, 1987 and which is incorporated herein by reference. Indicia means of the present invention are preferably disposed in rows disposed at an angle to the lateral direction, preferably at the same angle as the tape tabs 36, to allow angled fastening of the tape tab for optimized fit and for providing an angled primary line of tension. The indicia means 144 comprise a combination of different geometric shapes, colors, and objects, for example, rows and columns of teddy bears.

In a preferred embodiment of the present invention as is shown in FIG. 1, the closure system additionally comprises a waist closure system for providing a waist closure adjacent the front end edge 56 of the diaper 20. The waist closure anchors a portion of the span of the front end edge 56. Further, when the diaper 20 comprises a front elastic waist feature, the waist closure dynamically creates/maintains tension through the front elastic waist feature (i.e., through the elasticized waistband portion of the unitary waistcap/waistband 70). An exemplary example of a waist closure system is described in U.S. patent application Ser. No. 08/020,093, allowed, entitled "Absorbent Article With Fastening System Providing Dynamic Elasticized Waistband", filed by Weil, et al. on Feb. 19, 1993, which is incorporated herein by reference.

The waist closure anchors a portion of the span of the front end edge 56, preferably a portion of the extensible span of the front elastic waist feature, preferably the elasticized waistband portion of the unitary waistcap/waistband 70. (i.e., The first and second attachment components of the waist closure system act to anchor the positional relationship of the elasticized waistband portion with the elastic side panels 30.) The positional relationship of the elasticized waistband portion with the elastic side panels 30 (i.e., the geometric relationship between the anchor zones of the first attachment components 40) establishes a defined waist circumferential dimension adjacent the front end edge 56 which is distinct (longitudinally spaced) from the circumferential dimension established by the side closure formed by the primary fastening system. This distinct, defined waist circumferential dimension creates/maintains the required fit dimension(s) at the upper extremities (adjacent the front end edge 56) of the diaper 20. Thus, the waist closure system of the present invention can also be beneficial for use on diapers not employing an elastic waist feature (e.g., a waistshield or a nonextensible waist feature) so as to maintain a nonextensible fit at the front end edge 56 (upper edge) of the diaper 20. The anchoring also provides a means for transferring shear forces (tensions) between the front elastic waist feature and the elastic side panels so as to enhance the initial pretension created within the front elastic waist feature.

The waist closure also creates/maintains a line(s) of tension through the front elastic waist feature (i.e., the waistband portion 71 of the unitary waistcap/waistband 70). The waist closure contributes some portion of an initial pretension (having a vector component in the lateral direction) within the elasticized waistband portion that allows the elasticized waistband portion to snugly fit against the wearer's waist when initially fitted. The elasticized waistband portion maintains, during use, some portion of the pretension created within it by the waist closure. Since the elasticized waistband portion maintains some portion of the pretension created within it, the elasticized waistband portion can repeatedly elastically expand or contract with the motions of the wearer so as to snugly sustain the fit of the diaper against the wearer's waist throughout use. In particular, during wearing conditions, the elasticized waistband portion, in order to follow the movements of the wearer's waist, may have to contract to its untensioned state (i.e., the pretension goes to zero); however, because the attachment components remain engaged, the pretension will be reestablished within the elasticized waistband portion with further movement and activity by the wearer. (This is in contrast to most conventional elastic waist features that are not pretensioned such as to not be able to further contract to dynamically fit the wearer.) This initial pretensioning and maintenance of the tension thus results in reduced gapping and better sustained fit of the front elastic waist feature. Further, the lateral tension(s) created/maintained by the waist closure provide restoring forces within the front elastic waist feature that reduce or counteract the incidence of waistband "rollover". Thus, the waist closure system provides a closure about the waist of the wearer to improve the initial and dynamic fit and containment characteristics of the diaper.

As shown in FIG. 1, the waist closure system comprises at least one, preferably a pair of, first attachment components 40 and at least one second attachment component 42. As shown in FIG. 1, the first attachment components 40 are longitudinally aligned with the front elastic waist feature, preferably the elasticized waistband portion of the unitary waistcap/waistband 70, so that the tensions dynamically created/maintained by the waist closure system extends in and through the front elastic waist feature during use. Further, the attachment components of the waist closure system are longitudinally spaced from the tape tabs and the landing member of the primary fastening system to provide a distinct, defined waist circumferential dimension for the diaper and two distinct zones of tension. The line or zone of tension created by the primary fastening system (primary line of tension) secures the diaper on the wearer while the line or zone of tension dynamically created/maintained by the waist closure system dynamically maintains the upper waist closure during wear.

At least two anchor zones are created by the attachment components when the waist closure is formed. These two anchor zones are laterally spaced from each other with all or at least a portion of the front elastic waist feature positioned between the anchor zones. The lateral spacing of these anchor zones can be achieved in a number of different ways. For example, the lateral spacing between the anchor zones can be fixed by providing the waist closure system with a pair of first attachment components laterally spaced from each other and a second attachment component(s) that allows adjustable positioning with the first attachment components (e.g., the second attachment component(s) is relatively wide). In this embodiment, since the lateral spacing of the first attachment components is fixed, the lateral spacing of the first attachment components determines and sets the lateral spacing of the anchor zones. In an alternative embodiment, the waist closure system may comprise a pair of second attachment components laterally spaced from each other and a first attachment component(s) that allows adjustable positioning with the second attachment components (e.g., the first attachment component is relatively wide). In this embodiment, the lateral spacing of the anchor zones is determined by the size of the waist of the wearer and the overall dimension/shape of the diaper since the location of where the second attachment component 42 engages the first attachment components 40 depends upon the overlap of the back side panels 64 with the front side panels 62.

The preferred lateral spacing of the anchor zones is designed to allow passive activation of the waist closure when the side closure is formed, and to assure the maintenance of normal forces applied to the waist of the wearer to decrease the tendency of the front elastic waist feature to nonrecoverably rollover while providing an effective amount of stretch in the front elastic waist feature that improves the fit and containment of the diaper at the waist. In order to maintain normal forces within the front elastic waist feature that provide for recovery of the front elastic waist feature and minimize flipping out of the tensioned front elastic waist feature (i.e., nonrecoverable rollover), the lateral spacing of the anchor zones would desirably be kept to a minimum. However, in order to provide a maximum amount of stretch in the front elastic waist feature, the lateral spacing of the anchor zones would be desirably chosen to be at a maximum. Therefore, the lateral spacing of the anchor zones is thus chosen so as to balance the need for maintaining the normal forces with the need for providing an effective amount of stretch in the front elastic waist feature.

In the diaper embodiment shown in FIG. 1, the lateral spacing between the anchor zones (between the first attachment components 40) is at least about 25 mm. More preferably, the lateral spacing is at least about 50 mm. The lateral spacing of the first attachment components is most preferably between about 100 mm and about 200 mm. The lateral spacing of the anchor zones is determined by measuring the distance from the innermost line of securement (i.e., that line closest to the longitudinal centerline 67) of one anchor zone to the innermost line of securement of the other anchor zone with the front elastic waist feature in its contracted state. Thus, in the embodiment illustrated in FIG. 1, the lateral spacing is determined by measuring the distance from the innermost edge of one of the first attachment components to the innermost edge of the other first attachment component.

Each attachment component comprises a fastening means that engages a complementary fastening means for providing a waist closure, preferably a variable positioning, passively activated, waist closure. As used herein, the term "variable positioning" closure refers to a fastening system wherein at least one of the positions of the components can widely vary so as to allow the user to form a closure at a number of different locations. Thus, for example, one of the components may have a fixed location on the diaper (e.g., the lateral spacing between the first attachment components is fixed so as to provide for the pretensioning of the front elastic waist feature and the passive activation of the waist closure) while the other component allows for variable locations of attachment to the fixed component. This is in contrast to a "fixed" positioning closure which requires both of the mating elements to be fixed in position such that the components must be joined at a specific location each time the closure is formed (e.g., snaps and buckles). The waist closure system also provides a passively activated waist closure. By "passively activated", it is meant that a functional waist closure is achieved with little or no additional effort by the diaperer after a suitable initial body/leg fit (side closure) is achieved using the primary fastening system. Passive activation of the waist closure system requires the attachment components to not only engage each other so as to provide a secure anchor with little or no additional effort but also to be positioned on the diaper in an arrangement that creates/maintains the tensions within the front elastic waist feature.

As shown in FIG. 1, the attachment components preferably comprise mechanical closure elements. As used herein, the term "mechanical closure elements" describes fastening means which mechanically engage each other for providing a variable-position closure. Thus, the mechanical closure elements may comprise any of the well known means for achieving a variable-position closure by mechanical engagement such as "VELCRO" or other hook and loop fastening materials.

When the first attachment component 40 comprises a mechanical closure element, the second attachment component 42 may comprise "identical" complementary mechanical closure elements or "distinct" complementary mechanical closure elements. As used herein, the term "identical" complementary mechanical closure elements is used to define mechanical fastening systems wherein the engaging elements of the first component and the second component comprise the same configuration or structure that are interlocking. Examples of such systems are described in U.S. Pat. No. 4,322,875 entitled "Two Strip Materials Used For Forming Fasteners" issued to Brown, et al. on Apr. 16, 1982. The term "distinct" complementary mechanical closure elements is used herein to define mechanical fastening systems wherein the first component is different from the second component but is engageable therewith such as a hook fastening material and a loop fastening material. For example, if the second attachment component comprises a loop fastening material then the first attachment component will comprise a hook fastening material and vice versa.

As used herein, the term "hook fastening material" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary mechanical closure element such as a loop fastening material or another hook fastening material.

The hook fastening material is preferably intended to mechanically engage fibrous elements of a loop fastening material so as to provide a secure closure. Thus, a hook fastening material according to the present invention may be manufactured from a wide range of materials. Suitable materials include nylon, polyester, polypropylene, or any combination of these materials, or other materials as are known in the art. A suitable hook fastening material comprises a number of shaped engaging elements projecting from a backing such as the commercially available material designated "SCOTCHMATE" brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815 entitled "Disposable Diaper Having An Improved Fastening Device" issued to Scripps on Jul. 11, 1989, and which patent is incorporated herein by reference.

An especially preferred hook fastening material, as shown in FIG. 1, comprises an array of prongs formed of thermoplastic material. Hot melt adhesive thermoplastics, in particular polyester and polyamide hot melt adhesives, are particularly well suited for forming the prongs of the hook fastening material. The prongs are preferably manufactured using a modified gravure or a screen printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This preferred hook fastening material and methods and apparatus for making such a hook fastening material are more fully detailed in U.S. Pat. No. 5,058,247, entitled "Mechanical Fastening Prong" issued to Thomas and Blaney on Oct. 22, 1991; which patent is incorporated herein by reference.

A loop fastening material provides a plurality of fibrous elements that engage the engaging elements of a hook fastening material. The loop fastening material may be manufactured from a wide range of materials to provide fibrous elements, preferably loops. Such suitable materials include nylon, polyester, polypropylene, any combination of these materials, or other materials as are known in the art. A suitable loop fastening material comprises a number of fiber loops projecting from a backing such as the commercially available material designated "SCOTCHMATE" brand nylon woven loop No. SJ3401 available from Minnesota Mining and Manufacturing Company, St. Paul, Minn. Another commercially available loop fastening material comprises a tricot knit fabric having a plurality of nylon filament loops projecting from a backing of nylon such as the commercially available material designated "Guilford No. 16110" available from Guilford Mills of Greensboro, N.C. An exemplary inexpensive loop fastening material and a method of making such a loop fastening material are described in U.S. Pat. No. 5,032,122 entitled "Loop Fastening Material For Fastening Device and Method of Making Same", issued to Noel and Scripps on Jul. 16, 1991, which patent is incorporated herein by reference. A suitable loop fastening material may also be a woven or nonwoven fabric or any other type of fibrous material or loop material which are well known in the art. Examples of nonwoven materials suitable for use as a loop fastening material herein are discussed with respect to the materials useful as the topsheet 24 of the diaper 20. In a preferred embodiment, the second attachment component 42 comprises a loop fastening material formed by the nonwoven material of the topsheet 24.

The attachment components may alternatively comprise an adhesive attachment layer (a layer of adhesive material). Adhesives useful in the present invention are preferably pressure-sensitive adhesives formulated to adhere to a surface at ambient temperature by applying only light pressure. Particularly preferred adhesives for use herein as the adhesive attachment layer are hot melt pressure-sensitive adhesives as are known in the art. An exemplary hot-melt pressure-sensitive adhesive is a Kraton based adhesive with tacifiers and other additives such as marketed by Findley Adhesives, Inc. of Elm Grove, Wis. under the tradename Findley 990 or H-2085.

The attachment components may further comprise a combination adhesive/mechanical closure element. For example, the attachment components may comprise a combination fastener such as hook fastening material and an adhesive attachment layer juxtaposed with the hook fastening material or a mechanical closure element such as a hook fastening material having a layer of adhesive coated over a portion of the base or the hooks of the hook fastening material. An exemplary fastener having a combination mechanical/adhesive system is the pressure-sensitive adhesive fastener having a textured fastening surface such as is disclosed in U.S. Pat. No. 4,946,527 issued to Battrell on Aug. 7, 1990.

The attachment components may alternatively further comprise any other cohesive material or materials that are known in the art for providing a variable positioning fastener capable of being passively activated. For example, a cohesive strip or material can be foams, rubbers such as crepe or latex rubbers, other adhesives, or a high static vinyl material. A separable fastener of a high static vinyl material is more fully described in U.S. Pat. No. 4,979,613 issued to McLaughlin & Kleinsmith on Dec. 25, 1990.

While the attachment components preferably provide for variable positioning and passive activation, in alternative embodiments, the attachment components may comprise fixed position and/or user activated fasteners. Examples of such fasteners include snaps, hook and eye fasteners, studs, buttons, or the like.

The attachment components may comprise a separate element joined to the diaper or may be a unitary element with one of the other components of the diaper. For example, the topsheet 24 may be manufactured from a material (e.g., a nonwoven web), that is capable of mechanically engaging the other attachment component (e.g., a hook fastening material). Further, the backsheet 26 can be formed from a web having a textured pattern with a layer of adhesive coated over a portion of the backsheet surface to form a combination mechanical/adhesive fastener (attachment component) such as is shown in the hereinbefore referenced U.S. Pat. No. 4,946,527 to Battrell. In each of these cases, the attachment component is unitary with another component of the diaper. Alternatively, the attachment component may comprise a discrete strip or patch joined to the diaper. In a preferred embodiment shown in FIG. 1, each first attachment component 40 comprises a discrete separate patch of a hook fastening material joined to the backsheet 26 so as to form a portion of the outer surface 46 while the second attachment component 42 is a unitary element comprising a portion of the topsheet 24 in the second waist region 58.

Each first attachment component 40 comprises an about 12 mm wide (i.e., generally perpendicular to the longitudinal centerline 67) by about 19 mm patch of a hook fastening material. The first attachment components 40 are preferably positioned so as to have a lateral spacing of about 171 mm. Each first attachment component 40 is also spaced longitudinally from the front end edge 56. If the longitudinal spacing of the first attachment component (measured from the front end edge 56 of the diaper to the closest edge of the first attachment component 40) is too small, the first attachment component may be too high on the diaper and be in a position to contact the wearer's skin; if the longitudinal spacing is too great, the first attachment component may be so low as to allow some rollover of the front elastic waist feature. The first attachment components are preferably spaced from about 3 mm (⅛ inch) to about 15 mm (⅝ inch) from the front end edge 56, preferably from about 8 mm to about 10 mm. The hook fastening material used for the first attachment components 40 preferably comprises an array of thermoplastic prongs formed on a backing; the prongs of each hook fastening material most preferably being oriented with the engaging means at an angle to the lateral direction corresponding to the curvature or differential extensibility of the front elastic waist feature so that maximum tension is created in the front elastic waist feature or to the primary line of tension so as to be parallel to the primary line of tension. The waist closure system also comprises a single second attachment component 42 comprising a loop fastening material formed by a portion of the nonwoven material of the topsheet 24.

The diaper 20 additionally comprises a positioning patch 44 located subjacent the first attachment component 40. The positioning patch 44 raises the first attachment component 40 in the Z direction (thickness) to allow the first attachment component 40 to come in better contact with the second attachment component 42 and allow the waist closure system to more easily be closed (with less effort). Thus, the waist closure system is more effectively passively activated. The positioning patch 44 also provides a zone of increased flexural stiffness that reduces the tendency of the flexible front side panels 62 to fold over onto the first attachment components 40 thereby occluding the hooks from being secured during diaper application. Thus, the positioning patch 44 can comprise any element that provides a Z direction build up to the first attachment components 40. As shown in FIG. 1, the positioning patches 44 each comprise a rectangular-shaped piece of material positioned subjacent the first attachment component 40. While the positioning patches 44 may be positioned directly subjacent the first attachment components 40, the positioning patches 44 are preferably positioned between the topsheet 24 and the backsheet 26. In order to provide a flexurally stiff circumference about the waist of the wearer, the lateral edges of the positioning patches can be abutted to or slightly overlapped with the side edges of the material forming the front elastic waist feature. The positioning patches 44 preferably comprise a 38 mm wide by 32 mm long patch of elastomeric foam. More preferably, during manufacture of the diaper, the positioning patches 44 are formed of the same material as the elastic side panel member 82 with the elastic side panel member 82 of one diaper and the positioning patch 44 of the adjacent diaper being formed from the same segment of material that is then cut after the diaper is completed. Thus, the positioning patch 44 extends from the front end edge 56 longitudinally inward toward the lateral centerline 66.

In a preferred embodiment of the present invention, the diaper 20 further comprises elastic features to provide improved body conformity, fit, and comfort for the wearer. In one embodiment, the entire containment assembly of the diaper positioned outside of the area occupied by the absorbent core may be elastically extensible to allow for expansion of the body of the wearer in the zones of the wearer subject to movement during wear. A preferred material for such an overall elasticated product is the material described in U.S. Pat. No. 5,032,120 entitled "Disposable Absorbent Article Having Improved Leg Cuffs" issued to Freeland and Allen on Jul. 16, 1991. The material preferably comprises the three ply laminate described therein comprising a central laminate of elastomeric hot melt adhesive, such as that marketed by Findley Adhesives Corporation of Wauwautosa, Wis. under the tradename 198-338, positioned between two outboard lamina such as nonwoven fabrics. Alternatively, the material can be a stretch laminate such as a zero strain stretch laminate as are described hereinafter. Because of the economics of providing an overall elastomeric containment assembly, the diaper 20 is preferably provided with specific elastic features to accommodate the extremities of the wearer. In particular, the diaper 20 is provided with elastic side panels 30, elastic leg cuffs 32, and elastic waist features 34.

As shown in FIG. 2, the diaper 20 preferably comprises elastic leg cuffs 32 for providing improved containment of liquids and other body exudates and for accommodating movements of the wearer adjacent the legs. Each elastic leg cuff 32 may comprise several different embodiments. (The leg cuff can also be referred to as leg bands, side flaps, barrier cuffs, or elastic cuffs.) U.S. Pat. No. 3,860,003 entitled "Contractable Side Portions For A Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquid within the garment. U.S. Pat. No. 5,032,120, entitled "Disposable Absorbent Article Having Improved Leg Cuffs" issued to Freeland and Allen on Jul. 16, 1991, discloses a disposable diaper having improved elastic leg cuffs. Each of these patents are incorporated herein by reference. While each elastic leg cuff 32 may be configured so as to be similar to any of the leg bands, gasketing cuffs, side flaps, barrier cuffs, or elastic cuffs described above, it is preferred that each elastic leg cuff 32 comprise at least a barrier cuff 76 comprising a barrier flap 77 and a spacing elastic member 80 such as described in the above-referenced U.S. Pat. No. 4,909,803. In a preferred embodiment, the elastic leg cuff 32 additionally comprises a gasketing cuff 74 with one or more elastic strands 75 positioned outboard of the barrier cuff 76 such as described in the above-referenced U.S. Pat. No. 4,695,278. In an especially preferred embodiment, the barrier cuff is inflected so that the distal edge 79 of the barrier cuff 76 in the back waist region 52 is outboard of the proximal edge 78 to provide better fit and containment about the buttocks of the wearer. Such a configuration is described in more detail in U.S. Pat. No. 5,087,255 entitled "Absorbent Article Having Inflected Barrier Cuffs" issued to Simms on Feb. 11, 1992, which patent is incorporated herein by reference.

Figure 10:
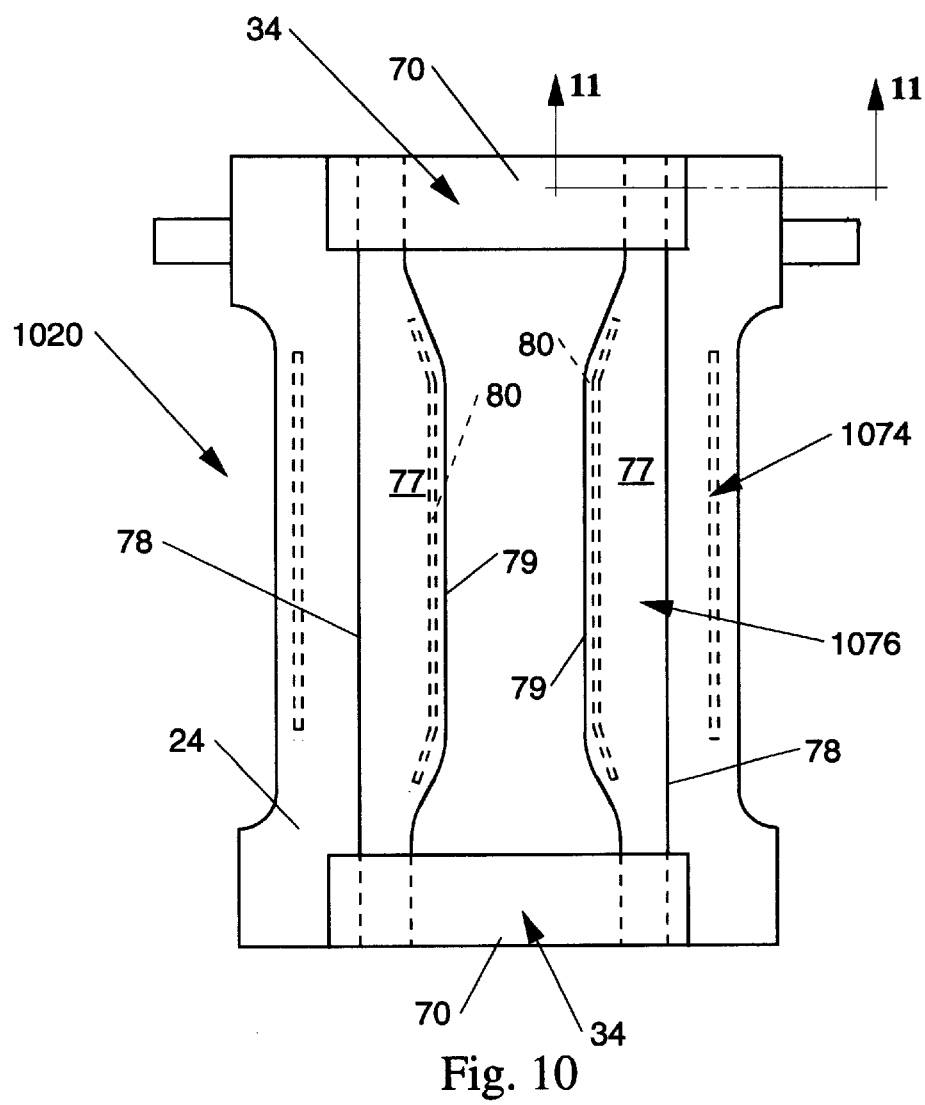
FIG. 10 is a plan view of a simplified diaper embodiment of the present invention with the inner surface facing the viewer to show the configuration of the barrier cuffs in a Z-folded arrangement adjacent each end edge.

FIG. 10 shows an alternative embodiment of an elastic leg cuff useful in the present invention. (FIG. 10 shows a conventional shape for a diaper in order to simplify the drawing.) Since the present invention requires a relatively narrow crotch area and absorbent core in order to fit within the low motion zone of the leg creases of the wearer, the barrier cuffs must be properly laterally spaced from each other in the crotch area and near the end edges while providing sufficient height to properly contain body exudates. Thus, current barrier cuff designs require a designer to compromise between the lateral spacing between the barrier cuffs and the height of the barrier cuffs. The present invention solves this dilemma by "Z"-folding and tacking down the barrier cuffs in the zones adjacent the elastic waist features in both the front waist region and the back waist region. The Z-folded barrier cuff design allows both sufficient lateral spacing of the barrier cuffs for the genitals in the front and for BM containment in the back as well as sufficient cuff height in the crotch area for good fit into the leg crease and good containment of body exudates. As shown in FIG. 10, the diaper 1020 is provided with a topsheet 24, a backsheet (not shown), an absorbent core (not shown), elastic leg cuffs each comprising a gasketing cuff 1074 and a barrier cuff 1076, and elastic waist features 34 each preferably comprising a unitary waistcap/waistband 70. The barrier cuffs 1076 each comprise a barrier flap 77 and a spacing elastic member 80, and have longitudinally opposed ends 1000, a proximal edge 78, and a distal edge 79. As shown in FIG. 10, the distal edge 79 is laterally spaced closer together in the crotch area of the diaper than in the waist areas (adjacent the ends 1000) especially when the diaper is in its contracted condition. This configuration is achieved by Z-folding the barrier flaps in the zones adjacent the end edges.

Figure 11:
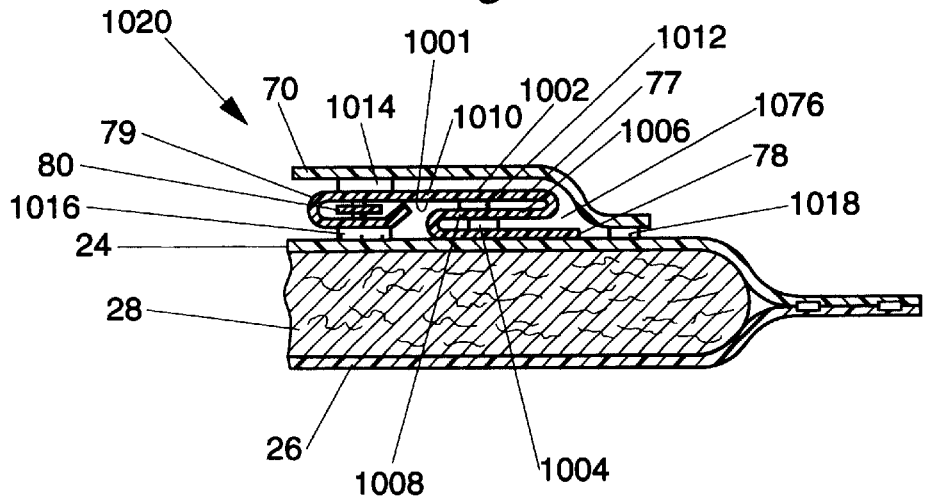
FIG. 11 is a cross-sectional view taken along line 11—11 in FIG. 10 showing the Z-folded segment of the barrier cuff in the back waist region.

FIG. 11 shows a cross-sectional view of the diaper 1020 of FIG. 10 taken along line 11—11. As shown in FIG. 11, the diaper 1020 comprises a topsheet 24; a backsheet 26; an absorbent core 28 positioned between the topsheet 24 and the backsheet 26; a barrier cuff 1076 having a proximal edge 78, a distal edge 79, an internal surface 1001, and an external surface 1002, and comprising a barrier flap 77 and a spacing elastic member 80; and a unitary waistcap/waistband 70. The proximal edge 78 is joined directly to the topsheet 24 by a proximal attachment member (not shown) such as dynamic mechanical bonds. The barrier flap 77 is folded laterally outwardly back upon itself such that a first segment 1004 and a second segment 1006 is formed with the exterior surface portion of the first segment directly facing the exterior surface portion of the second segment. The first segment 1004 is joined to the second segment 1006 by a first attachment member 1008 such an adhesive tack. The barrier flap 77 is also folded laterally inwardly back upon itself such that a third segment 1010 is formed with the interior surface portion of the third segment facing the interior surface portion of the second segment 1006. The third segment 1010 is joined to the second segment 1006 by a second attachment member 1012 such an adhesive tack. The third segment 1010 at the exterior surface is also preferably joined to the unitary waistcap/waistband 70 by a closure member 1014 such as an adhesive tack. The portion of the third segment adjacent then distal edge 79 is joined to the topsheet 24 by a second closure member 1016 such as an adhesive tack. The lateral edge of the unitary waistcap/waistband 70 is joined to the topsheet 24 by a side closure member 1018 such as an adhesive tack. Thus, the barrier flap 77, and thus the barrier cuff 1076, is Z-folded and tacked in a position that allows greater lateral spacing between the barrier cuffs adjacent the ends 1000 in the waist areas of the diaper. Further details as to the construction and materials useful for the various features of this invention are found in U.S. Pat. No. 4,695,278 issued to Lawson on Sep. 22, 1987; U.S. Pat. No. 4,938,755 issued to Foreman on Jul. 3, 1990; and U.S. Pat. No. 5,021,051 issued to Hiuke on Jun. 4, 1991; each of which is incorporated herein by reference.

The diaper 20 further comprises elastic waist features that provide improved fit and containment. Each elastic waist feature at least extends longitudinally outwardly from the respective waist edge of the absorbent core and generally forms at least a portion of the respective end edge. Thus, an elastic waist feature generally comprises that portion of the diaper at least extending from the waist edge of the absorbent core to the end edge of the containment assembly. Disposable diapers are generally constructed so as to have two elastic waist features, one positioned in the front waist region 50 (front elastic waist feature) and one positioned in the back waist region 52 (back elastic waist feature). While an absorbent article of the present invention can be constructed with a single elastic waist feature encircling the wearer such as on a training pant, the discussion regarding the elastic waist features will focus on absorbent articles having a pair of elastic waist features. Further, while each elastic waist feature or any of its constituent elements can comprise a separate element affixed to the containment assembly, both elastic waist features are, in a preferred embodiment, constructed as an extension of other elements of the containment assembly 22 such as the backsheet 26 or the topsheet 24, preferably both the topsheet 24 and the backsheet 26.

In a preferred embodiment of the present invention as shown in FIGS. 2 and 3, each elastic waist feature 34 comprises a unitary waistcap/waistband 70 such as is described in U.S. Pat. No. 5,026,364 entitled "Absorbent Article Having Unitary Waistcap and Waistband" issued to Robertson on Jun. 25, 1991, and which is incorporated herein by reference. The unitary waistcap/waistband 70 helps to keep the absorbent core 28 in close body contact in order to avoid gapping as well as controlling leakage at the waist. A single (unitary) piece of material serves both as an elasticized waistband and as a waistcap (barrier waist cuff). This single piece of material is referred to herein as a unitary waistcap/waistband 70. The unitary waistcap/waistband 70 serves two functions: it provides an elasticized waistband to enhance the fit of the diaper about the waist of the wearer and it provides a barrier waist cuff that is spaced away from the liquid-receiving surface of the diaper to form a channel which restrains, contains, and holds body exudates within the diaper (a waistcap). The unitary waistcap/waistband 70 is formed of an elastomeric material or materials including suitable elastic materials as are known in the art. Preferably, the unitary waistcap/waistband 70 is an elastomeric film laminate comprising an elastomeric film and a coverstock layer; more preferably, a laminate of a first coverstock layer, a second coverstock layer, and an elastomeric film positioned between the first coverstock layer and the second coverstock layer. The three materials are laminated together in any suitable manner as is known in the art. The unitary waistcap/waistband 70 is attached to the containment assembly 22, preferably directly to the topsheet 24, to form a portion of the inner surface 48 of the containment assembly 22. The unitary waistcap/waistband 70 is operatively associated with the containment assembly 22 by preferably securing it in an elastically contractible condition.

The front elastic waist feature and the back elastic waist feature each preferably has an arcuate shape so that forces transmitted through the elastic waist features are along a line at an angle to the body of the wearer as discussed herein. Thus, the front elastic waist feature preferably has a substantially arcuate concave shape to establish a line of tension matching the natural curve of the abdomen of the wearer and to provide comfortable fit about the wearer. The back elastic waist feature has a substantially arcuate convex shape to further fit the diaper into the lumbar curve of the back and to allow the tensional forces (the primary line of tension) to be directed downward toward the abdominal crease of the wearer so as to provide a continuous primary line of tension. Due to these shapes for the elastic waist features, each elastic waist feature typically has differential extensibility along the longitudinal axis when stretched in the lateral direction. The differential extensibility allows portions to laterally expand to a greater degree than other portions along the longitudinal axis. This differential extensibility provides an abdominally compliant front elastic waist feature that allows the front elastic waist feature to differentially shape, expand and move with the stomach of the wearer as the wearer moves, sits, and stands as well as directs the tensional forces in the back elastic waist feature at the appropriate angle along the wearer.

In an alternative embodiment, either or both of the elastic waist features may simply comprise an elasticized waistband comprising a portion of the topsheet, a portion of the backsheet, and an elastic member or members positioned between the topsheet and the backsheet. The elastic member may comprise a strip or strips (strands) of elastic material disposed in an arcuate configuration that matches the shape of the particular end edge to which it is disposed. Thus, the forces generated by the curved elastic waist member(s) have vector components in the longitudinal direction which contribute to sustained fit through better waistband contact with the wearer and less rollover.

Figure 3A:
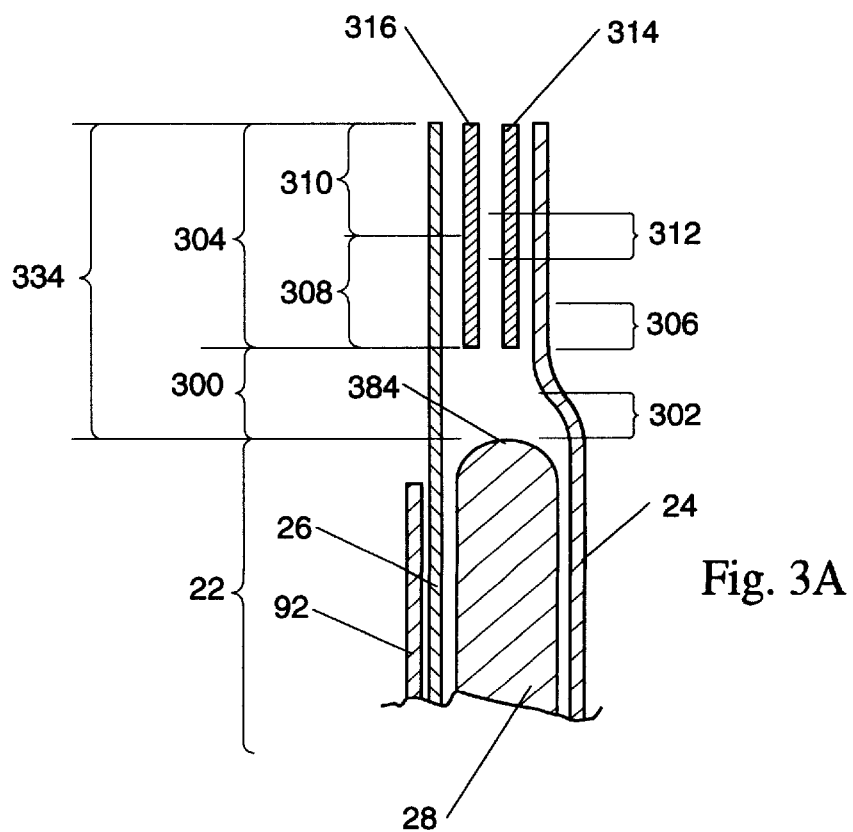
FIG. 3A is a fragmentary cross-sectional view of an alternative elastic waist feature embodiment taken through line 3—3 of FIG. 1 in the front waist region.

An example of another elastic waist feature useful in the present invention is the elastic waist feature 334 shown in FIG. 3A and disclosed in U.S. Pat. No. 5,151,092 entitled "Absorbent Article With A Dynamic Elastic Waist Feature Having A Predisposed Resilient Flexural Hinge" issued to Buell, Clear & Falcone on Sep. 29, 1992 and incorporated herein by reference. While the elastic waist feature 334 need only comprise an elasticized waistband and a flexural hinge zone joining the elasticized waistband with the contaiment assembly, the elastic waist feature 334 preferably comprises an interconnecting panel zone 300, a first flexural hinge zone 302 joining the interconnecting panel zone 300 with the containment assembly 22 adjacent the waist edge 384 of the absorbent core 28, an elasticized waistband 304, and a second flexural hinge zone 306 joining the elasticized waistband 304 with the interconnecting panel zone 300. The interconnecting panel zone 300 preferably provides a link between the elasticized waistband 304 and the absorbent core 28. The elasticized waistband 304 provides a member that maintains a defined area coverage, contacts the wearer, and is elastically extensible in a direction having a vector component in the lateral direction so as to dynamically fit against the wearer and to dynamically conform to the wearer so as to provide improved fit. The elasticized waistband 304 preferably comprises a shaping panel zone 308, a waistline panel zone 310, and a predisposed, resilient, waistband flexural hinge zone 312 joining the shaping panel zone 308 and the waistline panel zone 312.

In one embodiment of the elastic waist features described in U.S. Pat. No. 5,151,092 and as shown in FIG. 3A, the elastic waist feature 334 preferably comprises an interconnecting panel zone 300 comprising a portion of both the topsheet 24 and the backsheet 26; a first flexural hinge zone 302 and a second flexural hinge zone 306 formed from a structural discontinuity due to the absence of the absorbent core 28 from the interconnecting panel zone 300 or the absence of the elastic members and resilient members in the elasticized waistband 304. The elasticized waistband 304, while it may be constructed in a number of different configurations, preferably comprises a portion of the topsheet 24, a portion of the backsheet 26, this portion of the backsheet can be "mechanically prestrained" if desired; an elastomeric member 314, and a resilient member 316. In an especially preferred embodiment, the elastomeric member 314 is preferably positioned between the topsheet 24 and the backsheet 26 with the resilient member 316 preferably being positioned between the backsheet 26 and the elastomeric member 314. The waistband flexural hinge zone 310 is formed by a structural discontinuity in the bond pattern between the shaping panel zone 308 and the waistline panel zone 312 so that the elasticized waistband 304 will tend to more readily flexurally bend along the region in the pattern where there are fewer bonds.

In an alternative embodiment, the elastic waist feature comprises a relatively high edge compression stiffness interconnecting panel zone flexurally joined to the containment assembly; and an "expansive tummy panel" elasticized waistband flexurally joined to the interconnecting panel zone; a first flexural hinge zone flexurally joining the interconnecting panel zone with the contaiment assembly; and a second flexural hinge zone flexurally joining the elasticized waistband with the interconnecting panel zone. The elasticized waistband preferably has a deep "pentagon" shape to form an "expansive tummy panel". The elasticized waistband is longer (longitudinal dimension) to provide for the primary side closure to be formed below the abdominal crease in the low motion zone. This shape for the waistband provides a waistband that moves and expands with the wearer's stomach as well as differential lateral extensibility such that portions of the elasticized waistband adjacent the end edge are more extensible than adjacent portions farther from the end edge. The elasticized waistband is preferably constructed of a portion of the backsheet, a portion of the topsheet, an elastomeric member positioned between the topsheet and the backsheet, and a resilient member positioned between the backsheet and the elastomeric member. The elastomeric member preferably comprises an elastomeric foam or elastomeric film (or stretch laminate) while the resilient member preferably comprises a nonwoven layer. The elasticized waistband preferably comprises a stretch laminate so that the elasticized waistband is capable of expanding beyond the original planar state of the diaper. This stretch laminate, preferably a mechanically stretched, pretensioned, stretch laminate allows for expansion of the elasticized waistband well beyond the dimensions of the circumference of the diaper formed by the primary closure system and beyond the initial dimension of the end edge (beyond the planar state of the diaper itself). (i.e., The elasticized waistband is capable of expanding well beyond the dimension of the circumference of the fixed dimension of the side closure (even beyond the dimension of the materials initially forming the diaper) so as to follow the wearer's stomach movements.) The stretch laminate can also be activated by mechanically stretching the stretch laminate at an angle to the longitudinal direction to provide differential stretch. This expansion can also be accomplished by or enhanced by "windowing" the elastic waist feature. The elasticized waistbands are preferably designed to have force/extension characteristics such that the extension forces are less than or equal to about 400 grams$_f$, preferably less than or equal to about 350 grams$_f$, and more preferably less than or equal to about 300 gramsf at extensions of between about 25 mm (1 inch) and about 50 mm (2 inches), more preferably between about 25 mm (1 inch) and about 76 mm (3 inches).

The diaper 20 further also preferably comprises elastic side panels 30 disposed in the back waist region 52. (As used herein, the term "disposed" is used to mean that an element (s) of the diaper is formed (joined and positioned) in a particular place or position as a unitary structure with other elements of the diaper or as a separate element joined to another element.) The elastic side panels provide an elastically extensible feature that provides a more comfortable and contouring fit by initially conformably fitting the diaper to the wearer and sustaining this fit throughout the time of wear well past when the diaper has been loaded with exudates since the elastic side panels allow the sides of the diaper to expand and contract. Further, the elastic side panels develop and maintain wearing forces (tensions) and enhance the tensions developed and maintained by the closure system to maintain the diaper on the wearer and enhance the fit. The elastic side panels especially assist in maintaining the angled primary line of tension formed by the primary fastening system; allowing the diaper to conformably fit over the hips of the wearer where there is dynamic motion, and initially pretensioning the front elastic waist feature since the diaperer typically stretches the elastic side panels when applying the diaper on the wearer so that when the elastic side panels contract, tension is transmitted from the elastic side panels through the waist closure system into the front elastic waist feature. The elastic side panels further provide more effective application of the diaper since even if the diaperer pulls one elastic side panel further than the other during application (asymmetrically), the diaper will "self-adjust" during wear. While the diaper 20 of the present invention preferably has the elastic side panels 30 disposed in the back waist region 52; alternatively, the diaper 20 may be provided with elastic side panels disposed in the front waist region 50 or in both the front waist region 50 and the back waist region 52.

The elastic side panels 30 may be constructed in a number of configurations. For example, the elastic side panels 30 may comprise a separate elastically extensible material or laminate joined to the containment assembly 22 or may be a unitary stretch laminate formed by operatively associating an elastic side panel member with the containment assembly. Examples of diapers with elastic side panels useful in the present invention are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaffara, et al. on May 3, 1983; U.S. Pat. No. 4,938,753 issued to Van Gompel, et al. on Jul. 3, 1990; and the hereinbefore referenced U.S. Pat. No. 5,151,092 issued to Buell, et al. on Sep. 29, 1992; each of which are incorporated herein by reference.

In a preferred embodiment as is shown in FIG. 1, the elastic side panels 30 comprise an elastic side panel member 82 joined to the containment assembly 22 in the back side panel 64 (preferably between the topsheet 24 and the backsheet 26). The elastic side panel member 82 is joined in a substantially untensioned condition with the resultant laminate being subjected to mechanical stretching sufficient to permanently elongate the nonelastic components (the topsheet 24 and the backsheet 26) and then allowed to return to its substantially untensioned condition. The preferred elastic side panels 30 thus comprise a "zero strain" stretch laminate as are discussed more fully in U.S. Pat. No. 5,151,092. As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically extensible, at least up to the point of initial stretching, in the direction of initial stretching. (Alternatively, the elastic side panels could comprise pretensioned stretch laminates formed by operatively associating the elastomeric component to the nonelastic component in a tensioned condition and then subjecting the resultant laminate to mechanical stretching.) Preferred examples of zero strain stretch laminates and pretensioned stretch laminates are disclosed in the above-referenced U.S. Pat. No. 5,151,092.

Particularly preferred methods and apparatus used for making "zero strain" stretch laminates out of a topsheet, a backsheet, and an elastomeric member positioned between the same, use meshing corrugated rolls to mechanically stretch the components. A discussion of suitable apparatus and methods for mechanically stretching portions of a diaper is contained in U.S. Pat. No. 5,167,897 entitled "Method For Incrementally Stretching a Zero Strain Stretch Laminate Web to Impart Elasticity Thereto" issued to Weber, et al. on Dec. 1, 1992; and U.S. Pat. No. 5,156,793 entitled "Method For Incrementally Stretching Zero Strain Stretch Laminate Web in a Non-Uniform Manner to Impart A Varying Degree of Elasticity Thereto" issued to Buell, et al. on Oct. 20, 1992; each of which are incorporated herein by reference.

In a preferred embodiment of the present invention, the elastic side panels 30 are mechanically stretched so that the stretch laminate is extensible at an angle to the lateral direction (i.e., the elastic side panels are elastically extensible in a direction having a vector component in the longitudinal direction). Preferably, the elastic side panels 30 can be stretched an angle from about 5° to about 60°, preferably from about 5° to about 30°, more preferably between about 10° and about 25°, most preferably about 20° to the lateral direction (machine direction) of the diaper 20. This angled activation allows the elastic side panels 30 to form forces at an angle to the body to enhance the formation of an angled primary line of tension. This angled activation is accomplished by orienting the corrugation of the meshing corrugated rolls at the appropriate angle to the machine direction so as to produce elastic extensibility in a line at an angle to the body. (For a more complete discussion of angled activation of the stretch laminates, see U.S. Pat. No. 5,156,793).

The elastic side panel members 82 may take on a number of different sizes, shapes, configurations, and materials. For example, the elastic side panels may be formed from one or a plurality of elastic side panel members operatively associated in each side panel; the elastic side panel members may have varying widths and lengths; or the elastic side panel members may comprise relatively narrow strands of elastomeric material or a larger area of a elastomeric patch. One elastomeric material which has been found to be especially suitable for use as the elastic side panel member (especially for "zero strain" stretch laminates) is an elastomeric foam having an elongation to break of at least about 400% and an extension force of about 200 g/in of sample width at 50% extension of its own strain length. Other suitable elastomeric materials for use as the elastic side panel members include "live" synthetic or natural rubber, other synthetic or natural rubber foams, elastomeric films (including heat shrinkable elastomeric films), elastomeric scrim, elastomeric woven or nonwoven webs, elastomeric composites such as elastomeric laminates, or the like.

While the elastic side panel member 82 may longitudinally extend through the entire length of the back side panel 56, as shown in FIG. 1, the elastic side panel member 82 comprises a patch of elastomeric material (elastomeric patch) that preferably extends through only a portion of the longitudinal length of the back side panel 56 so as to form an extension panel 146. As shown in FIG. 1, the extension panel 146 has also been mechanically stretched at least to a degree to be extensible (i.e., the materials that make up the extension panel have been strained or permanently elongated). The extension panel allows this portion of the back side panel 56 to effectively elongate (yield) when the elastic side panel 30 is extended, without generating excessive tension forces near the leg region of the wearer that could cause skin irritation or red mark the legs. (Without the extension panels, tensional forces would be concentrated along a line through the back side panel when the elastic side panel is extended that could indent, rub, or chafe the skin of the wearer.) While there are a number of ways to strain the extension panel, the extension panel is preferably strained in the same manner and and the same time as the mechanical stretching performed on the elastic side panels. (Alternatively, the extension panel may be strained at a different angle from the elastic side panel to better relieve stress along the leg; such as being strained perpendicular to the direction of mechanical stretching of the elastic side panel.) While the extension panel may be formed from a number of different materials, in a preferred embodiment, the extension panel is formed from the portions of the topsheet and the backsheet in the back side panel.

Figure 14:
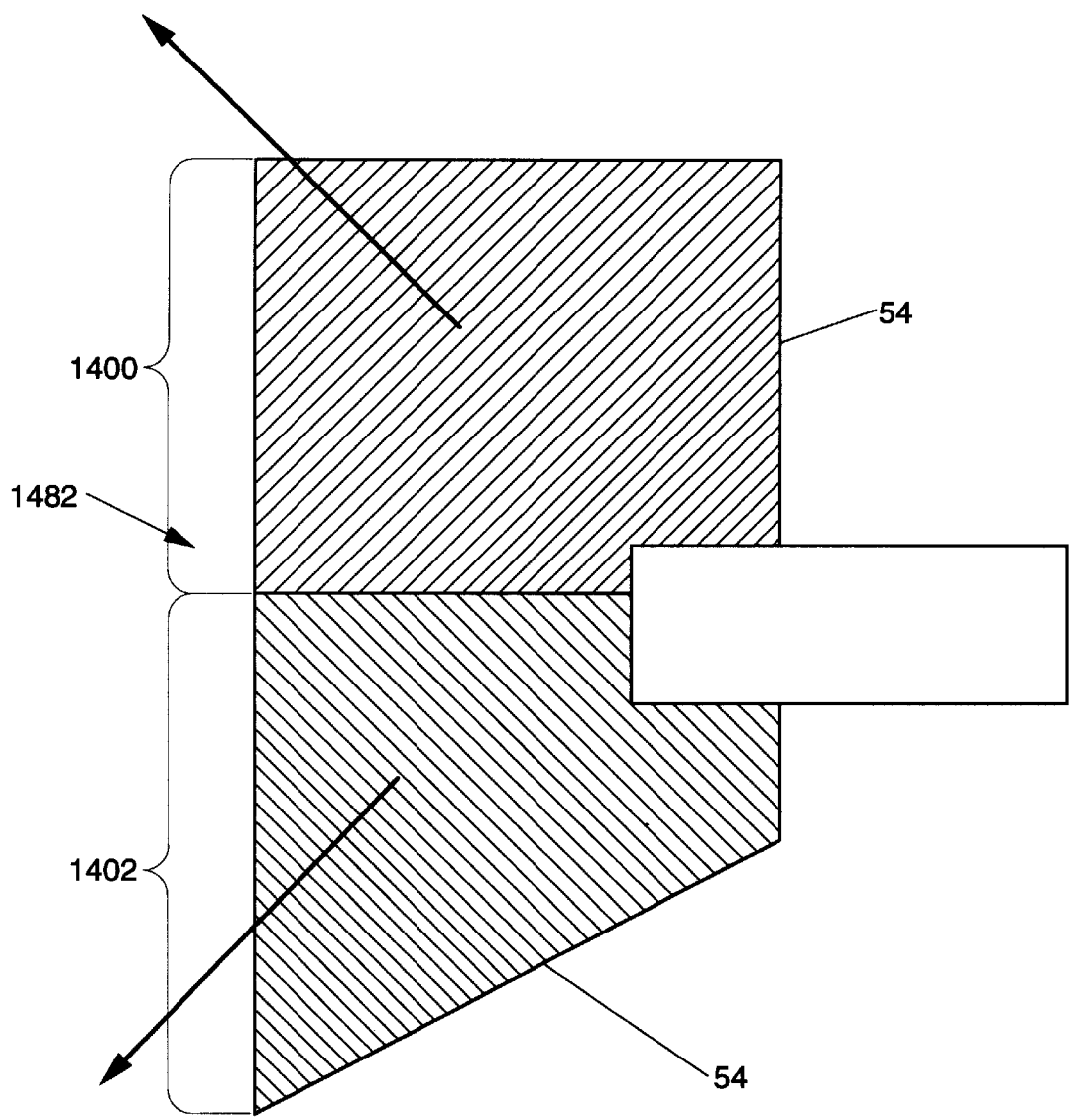
FIG. 14 is a plan view of an alternative elastic side panel configuration for the present invention.

In an alternative embodiment of the present invention as is shown in FIG. 14, the elastic side panel member 1482 may extend through the entire length of the back side panel 56. The elastic side panel member 1482 is preferably mechanically stretched in two different directions to provide expansion towards the waist (the top arrow in FIG. 14) and towards the legs (the bottom arrow of FIG. 14). Thus, a first portion 1400 of the elastic side panel member 1482 forms the elastic side panel 30 and a second portion 1402 forms a segment of the elastic leg cuff 1432. While the boundary between the zones of different extensibility may be positioned anywhere along the elastic side panel member, as shown in FIG. 14, the position of the tape tab preferably determines the boundary between the zones of different extensibility so that the tension lines are each activated by the tape tab. The first portion of the elastic side panel member is preferably activated at the angles discussed herein with respect to the elastic side panels such that an angled primary line of tension is formed. The second portion of the elastic side panel member is preferably activated at an angle to the line of activation of the first portion, preferably perpendicular to the line of activation of the first portion, so that the elastic side panel members form an elasticized thigh panel capable of elastically extending along the longitudinal edge of the containment assembly. The elasticized thigh panels enhance fit and containment in the areas about the legs. A more detailed discussion of a diaper having elasticized thigh panels is contained in U.S. patent application Ser. No. 07/951,608, entitled "Absorbent Article With Dynamic Elastic Leg Feature Comprising Elasticized Thigh Panels" filed by Clear, et al. on Sep. 25, 1992.

In a preferred embodiment of the present invention, the elastic side panel member 82 is substantially continuously bonded to both the topsheet 24 and the backsheet 26 using an adhesive. A glue applicator may be used to apply a substantially uniform and continuous layer of adhesive to the backsheet 26 and/or the topsheet 24 and those predetermined areas where the substantially untensioned elastic side panel member 82 will be placed. In a particularly preferred embodiment, the adhesive selected is stretchable and the glue applicator comprises a melt blown applicating system such as Model No. GM-50-2-1-GH as available from J&M Laboratories of Gainsville, Ga. Alternatively, the elastic side panel member 82 and any other components comprising the "zero strain" portions of the diaper 20 may be intermittently or continuously bonded to one another using unheated adhesive, heat bonding, pressure bonding, ultrasonic bonding, dynamic mechanical bonding, or any other method as is known in the art.

The diaper 20 is preferably applied to the wearer by positioning the back waist region 52 under the wearer's back and drawing the remainder of the diaper between the wearer's legs so that the front waist region 50 is positioned across the front of the wearer. The tab portion 124 of one of the tape tabs 36 is then released from the release portion 140. The first fastening component 37 on the tape tab 36 is secured to the second fastening component 39 on the landing member 38 to affect the side closure so that a primary line of tension is established about the wearer at an angle to the lateral direction. The other tape tab is then secured in a similar manner. The elastic side panels 30 and the back elastic waist feature will typically be extended in tension during this operation so as to conform to the size and shape of the wearer. In the preferred embodiment of the present invention, when the side closures are formed, the waist closure is also "automatically" formed (i.e., the waist closure is passively activated). The waist closure is formed by the engagement of the first attachment components 40 with the second attachment component 42. With the formation of the waist closure, the front elastic waist feature is pretensioned so as to provide the fit and containment benefits described herein. Thus, the absorbent core is positioned within the low motion zone of the wearer and the diaper is anchored in its ultimate, sustainable wearing position by the angled primary line of tension formed through the back elastic waist feature through the elastic side panels and through the primary fastening system. The primary line of tension also anchors the absorbent core below the abdominal crease. The portions of the diaper outside of the low motion zone are primarily elastically extensible and compliant to fit the changing dimensions of the wearer with the front elastic waist feature intended to prevent rollover, sagging and gapping. Thus, the diaper remains in its initial fit position and does not sag, gap, slide/slip on the wearer during use.

FIG. 9 shows an alternative embodiment of a disposable absorbent article of the present invention. The disposable absorbent article of FIG. 9 preferably comprises a pant-type garment (training pant 920) having closed side seams 900 so that the wearer pulls the pant up on the body rather than being secured with a closure system. (Alternatively, the absorbent article can be provided with a closure system such as that described herein rather than side seams.) The training pant 920 may be used as a training pant or as a diaper. The training pant 920 comprises a containment assembly 922 comprising a first outer covering layer 924, a second outer covering layer 926, side seams 900, elastic leg cuffs 932, an elastic waist feature 934, and an absorbent core 928.

The containment assembly 922 has the general shape of an undergarment of the type commonly worn as panties or training pants. The containment assembly 922 preferably comprises woven or nonwoven fabrics which are elastically extensible to provide overall elasticity for the training pant 920. The body of the containment assembly 922 may comprise a number of different materials as are known in the art including elastomeric nonwovens and laminates of elastomeric materials and nonwovens mechanically stretched or stretchable. Elastic is secured about the leg and waist openings to form elastic leg cuffs 932 and an elastic waist feature 934 to further securely hold the training pant in place.

The absorbent core 928 is preferably the absorbent core of the present invention such as that shown in FIG. 5 or alternatively in FIGS. 7A, 7B, 7C or 7D. The absorbent core 938 thus fits within the low motion zone and is anchored in the low motion zone by the overall elastication of the training pant 920. The absorbent core 928 may be positioned between the first outer covering layer 924 and the second outer covering layer 926, or the absorbent core 28 may be formed as a separate absorbent assembly comprising a topsheet, the absorbent core, and a backsheet, with the absorbent assembly secured in the training pant to the first outer covering layer 924. An exemplary example of a training pant assembly is more fully described in U.S. patent application Ser. No. 07/795,560, allowed, entitled "Elasticized Disposable Training Pant and Method of Making the Same", filed by Hasse, et al. on Nov. 21, 1991, incorporated herein by reference.

Flexure Bending Test

The flexure bending test is similar to the flexure bending test described in U.S. Pat. No. 5,151,092 issued to Buell, Clear & Falcone on Sep. 29, 1992. The portion of the specification of U.S. Pat. No. 5,151,092 describing the flexure bending test and the equipment used therein is hereby incorporated herein by reference.

The sample to be tested is taken from the tape tab materials as positioned on the diaper (e.g., when the tab portion 124 is to be tested, the material has the first fastening element thereon). The sample is at a minimum 16 mm long (longitudinal direction), preferably 25 mm or any length available, and 50 mm wide (lateral direction). The sample is centered on the supporting rods.

The test is run according to the procedures described except that the deflection force at 4 mm and 5 mm, for each cycle, is determined on the extension force curve (the upper curve). The extension deflection forces are averaged to calculate a cycle extension deflection force. The average of both cycle extension deflection forces for each sample determines the sample extension defection force. The bending flexure extension force for the material is the average of the value of the sample extension deflection force for the 10 samples.

While particular embodiments of the present invention have been illustrated and described, it would be obvious to those skilled in the art that various other changes and modifications can be made without departing from the spirit and scope of the invention. It is therefore intended to cover in the dependent claims all such changes and modifications that are within the scope of this invention.

What is claimed is:

1. An absorbent article comprising:

a liquid pervious topsheet;

a liquid impervious backsheet joined with said topsheet;

an absorbent core positioned between said topsheet and said backsheet; and a barrier cuff comprising a barrier flap and a spacing elastic member operatively associated with said barrier flap, each said barrier flap having longitudinally opposed ends, a proximal edge, a distal edge, a first surface, and a second surface, said proximal edge of said barrier flap being joined to said topsheet, a first portion of said barrier flap adjacent each of said ends being folded laterally outwardly back upon itself to form a first segment and a second segment, a second portion of said barrier flap adjacent each of said ends being folded laterally inwardly back upon itself at said second segment to form a third segment, said third segment including said distal edge, a portion of said third segment adjacent said distal edge being secured to said topsheet by a closure member positioned between said third segment and said topsheet laterally inwardly from said proximal edge so as to form a Z-folded barrier cuff adjacent said ends of each said barrier flap.

2. The absorbent article of claim 1 wherein said first segment is joined to said second segment by a first attachment member.

3. The absorbent article of claim 2 wherein said second segment is joined to said third segment by a second attachment member.

4. The absorbent article of claim 3 wherein said first attachment member, said closure member, and said second attachment member each comprises an adhesive tack.

5. An absorbent article having end edges and longitudinal edges, the absorbent article comprising:

a liquid pervious topsheet;

a liquid impervious backsheet joined with said topsheet;

an absorbent core positioned between said topsheet and said backsheet;

a barrier cuff comprising a barrier flap and a spacing elastic member operatively associated with said barrier flap, each said barrier flap having longitudinally opposed ends, a proximal edge, a distal edge, a first surface, and a second surface, said proximal edge of said barrier flap being joined to said topsheet, a first portion of said barrier flap adjacent each of said ends being folded laterally outwardly back upon itself to form a first segment and a second segment, a second portion of said barrier flap adjacent each of said ends being folded laterally inwardly back upon itself at said second segment to form a third segment, said third segment including said distal edge, a portion of said third segment adjacent said distal edge being secured to said topsheet by a closure member positioned between said third segment and said topsheet laterally inwardly from said proximal edge so as to form a Z-folded barrier cuff adjacent said ends of each said barrier flap; and a unitary waistcap/waistband joined to said topsheet adjacent each end edge of the absorbent article, each of said unitary waistcap/waistband being positioned over one of said ends of each said barrier cuff.

6. The absorbent article of claim 5 wherein said third segment is joined to said unitary waistcap/waistband by a second closure member.

7. The absorbent article of claim 6 wherein said first segment is joined to said second segment by a first attachment member.

8. The absorbent article of claim 7 wherein said second segment is joined to said third segment by a second attachment member.

9. The absorbent article of claim 8 wherein said closure member, said second closure member, said first attachment member, and said second attachment member each comprises an adhesive tack.

\* \* \* \* \*